US007211390B2

(12) United States Patent
Rothberg et al.

(10) Patent No.: US 7,211,390 B2
(45) Date of Patent: May 1, 2007

(54) METHOD OF SEQUENCING A NUCLEIC ACID

(75) Inventors: Jonathan M. Rothberg, Guilford, CT (US); Joel S. Bader, Paris (FR); Scott B. Dewell, New Haven, CT (US); Keith McDade, Clinton, CT (US); John W. Simpson, Madison, CT (US); Jan Berka, New Haven, CT (US); Christopher M. Colangelo, Pawcatuck, CT (US)

(73) Assignee: 454 Life Sciences Corporation, Branford, CT (US)

( * ) Notice: Subject to any disclaimer, the term of this patent is extended or adjusted under 35 U.S.C. 154(b) by 412 days.

(21) Appl. No.: 10/788,529

(22) Filed: Feb. 26, 2004

(65) Prior Publication Data

US 2004/0248161 A1    Dec. 9, 2004

(51) Int. Cl.
C12Q 1/68 (2006.01)
C12P 19/34 (2006.01)
C07H 21/04 (2006.01)

(52) U.S. Cl. ............. 435/6; 435/91.1; 435/91.2; 536/24.3

(58) Field of Classification Search ............... None
See application file for complete search history.

(56) References Cited

U.S. PATENT DOCUMENTS

| | | |
|---|---|---|
| 4,402,568 A | 9/1983 | Kulich et al. ............. 350/96.16 |
| 4,683,195 A | 7/1987 | Mullis et al. |
| 4,683,202 A | 7/1987 | Mullis |
| 4,811,218 A | 3/1989 | Hunkapiller et al. |
| 4,822,746 A | 4/1989 | Walt |
| 4,863,849 A | 9/1989 | Melamede |
| 4,965,188 A | 10/1990 | Mullis et al. |
| 4,971,903 A | 11/1990 | Hyman |
| 5,114,864 A | 5/1992 | Walt et al. |
| 5,114,984 A | 5/1992 | Branch et al. |
| 5,143,853 A | 9/1992 | Walt |
| 5,171,534 A | 12/1992 | Smith et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,298,741 A | 3/1994 | Walt et al. |
| 5,302,509 A | 4/1994 | Cheeseman |
| 5,320,814 A | 6/1994 | Walt et al. |
| 5,354,825 A | 10/1994 | Klainer et al. |
| 5,405,746 A | 4/1995 | Uhlen |
| 5,429,807 A | 7/1995 | Matson et al. |
| 5,436,327 A | 7/1995 | Southern et al. |
| 5,445,934 A | 8/1995 | Fodor et al. |
| 5,445,971 A | 8/1995 | Rohr |
| 5,480,723 A | 1/1996 | Klainer et al. |
| 5,512,490 A | 4/1996 | Walt et al. |
| 5,525,464 A | 6/1996 | Drmanac et al. |
| 5,534,424 A | 7/1996 | Uhlen et al. |
| 5,604,097 A | 2/1997 | Brenner |
| 5,633,972 A | 5/1997 | Walt et al. |
| 5,648,245 A | 7/1997 | Fire et al. |
| 5,700,637 A | 12/1997 | Southern |
| 5,700,897 A | 12/1997 | Klainer et al. |
| 5,714,320 A | 2/1998 | Kool |
| 5,716,785 A | 2/1998 | Van Gelder et al. |
| 5,728,529 A | 3/1998 | Metzker et al. |
| 5,744,305 A | 4/1998 | Fodor et al. |
| 5,750,341 A | 5/1998 | Macevicz |
| 5,770,367 A | 6/1998 | Southern et al. |
| 5,780,231 A | 7/1998 | Brenner |
| 5,795,716 A | 8/1998 | Chee |
| 5,800,992 A | 9/1998 | Fodor et al. |
| 5,814,524 A | 9/1998 | Walt et al. |
| 5,821,058 A | 10/1998 | Smith et al. |
| 5,830,662 A | 11/1998 | Soares et al. |
| 5,834,252 A | 11/1998 | Stemmer et al. |
| 5,837,832 A | 11/1998 | Chee et al. |
| 5,846,721 A | 12/1998 | Soares et al. |

(Continued)

FOREIGN PATENT DOCUMENTS

EP    0 373 203    8/1994

(Continued)

OTHER PUBLICATIONS

Baner et al., "Signal amplification of padlock probes by rolling circle replication." Nucleic Acids Research 26(22): 5073-5078 (1998).

(Continued)

Primary Examiner—Young J. Kim
(74) Attorney, Agent, or Firm—Ivor R. Elrifi, Esq.; Mintz Levin Cohn Ferris Glovsky and Popeo PC

(57) ABSTRACT

Disclosed herein are methods and apparatuses for sequencing a nucleic acid. In one aspect, the method includes annealing a population of circular nucleic acid molecules to a plurality of anchor primers linked to a solid support, and amplifying those members of the population of circular nucleic acid molecules which anneal to the target nucleic acid, and then sequencing the amplified molecules by detecting the presence of a sequence byproduct such as pyrophosphate.

30 Claims, 8 Drawing Sheets

U.S. PATENT DOCUMENTS

| | | |
|---|---|---|
| 5,846,727 A | 12/1998 | Soper et al. |
| 5,851,772 A | 12/1998 | Mirzabekov et al. |
| 5,854,033 A | 12/1998 | Lizardi |
| 5,856,104 A | 1/1999 | Chee et al. |
| 5,861,242 A | 1/1999 | Chee et al. |
| 5,871,697 A | 2/1999 | Rothberg et al. |
| 5,871,928 A | 2/1999 | Fodor et al. |
| 5,882,874 A | 3/1999 | Fisher |
| 5,888,819 A | 3/1999 | Goelet et al. |
| 5,891,636 A | 4/1999 | Van Gelder et al. |
| 5,900,481 A | 5/1999 | Lough et al. |
| 5,919,673 A | 7/1999 | Wong et al. |
| 5,928,905 A | 7/1999 | Stemmer et al. |
| 5,962,228 A | 10/1999 | Brenner |
| 5,974,164 A | 10/1999 | Chee |
| 6,013,440 A | 1/2000 | Lipshutz et al. |
| 6,013,445 A | 1/2000 | Albrecht et al. |
| 6,013,449 A | 1/2000 | Hacia et al. |
| 6,023,540 A | 2/2000 | Walt et al. |
| 6,027,880 A | 2/2000 | Cronin et al. |
| 6,040,138 A | 3/2000 | Lockhart et al. |
| 6,040,193 A | 3/2000 | Winkler et al. |
| 6,050,719 A | 4/2000 | Winkler et al. |
| 6,054,270 A | 4/2000 | Southern |
| 6,080,585 A | 6/2000 | Southern et al. |
| 6,114,114 A | 9/2000 | Seilhamer et al. |
| 6,133,436 A | 10/2000 | Koster et al. |
| 6,136,543 A | 10/2000 | Anazawa et al. |
| 6,146,593 A | 11/2000 | Pinkel et al. |
| 6,150,095 A | 11/2000 | Southern et al. |
| 6,156,501 A | 12/2000 | McGall et al. |
| 6,200,737 B1 | 3/2001 | Walt et al. |
| 6,210,891 B1 | 4/2001 | Nyren et al. |
| 6,210,896 B1 | 4/2001 | Chan |
| 6,210,910 B1 | 4/2001 | Walt et al. |
| 6,218,111 B1 | 4/2001 | Southern et al. |
| 6,221,653 B1 | 4/2001 | Caren et al. |
| 6,225,061 B1 | 5/2001 | Becker et al. |
| 6,228,575 B1 | 5/2001 | Gingeras et al. |
| 6,238,862 B1 | 5/2001 | McGall et al. |
| 6,242,180 B1 | 6/2001 | Chee |
| 6,255,476 B1 | 7/2001 | Vinayak et al. |
| 6,258,568 B1 | 7/2001 | Nyren |
| 6,263,286 B1 | 7/2001 | Gilmanshin et al. |
| 6,266,459 B1 | 7/2001 | Walt et al. |
| 6,280,950 B1 | 8/2001 | Lipshutz et al. |
| 6,285,807 B1 | 9/2001 | Walt et al. |
| 6,306,597 B1 | 10/2001 | Macevicz |
| 6,306,643 B1 | 10/2001 | Gentalen et al. |
| 6,307,039 B1 | 10/2001 | Southern |
| 6,309,823 B1 | 10/2001 | Cronin et al. |
| 6,327,410 B1 | 12/2001 | Walt et al. |
| 6,333,155 B1 | 12/2001 | Lockhart et al. |
| 6,342,355 B1 | 1/2002 | Hacia et al. |
| 6,344,316 B1 | 2/2002 | Lockhart et al. |
| 6,355,420 B1 | 3/2002 | Chan |
| 6,355,431 B1 | 3/2002 | Chee et al. |
| 6,368,799 B1 | 4/2002 | Chee |
| 6,377,721 B1 | 4/2002 | Walt et al. |
| 6,396,995 B1 | 5/2002 | Stuelpnagel et al. |
| 6,406,845 B1 | 6/2002 | Walt et al. |
| 6,410,229 B1 | 6/2002 | Lockhart et al. |
| 6,429,027 B1 | 8/2002 | Chee et al. |
| 6,440,677 B2 | 8/2002 | Lipshutz et al. |
| 6,468,744 B1 | 10/2002 | Cronin et al. |
| 6,482,593 B2 | 11/2002 | Walt et al. |
| 6,519,583 B1 | 2/2003 | Koleszar et al. |
| 6,544,732 B1 | 4/2003 | Chee et al. |
| 6,548,257 B2 | 4/2003 | Lockhart et al. |
| 6,576,425 B2 | 6/2003 | McGall et al. |
| 6,607,887 B2 | 8/2003 | Chee |
| 6,611,828 B1 | 8/2003 | Koleszar et al. |
| 6,620,584 B1 | 9/2003 | Chee et al. |
| 6,643,634 B2 | 11/2003 | Koleszar et al. |
| 6,663,832 B2 | 12/2003 | Lebl et al. |
| 6,667,159 B1 | 12/2003 | Walt et al. |
| 6,705,754 B2 | 3/2004 | Winkler et al. |
| 6,720,007 B2 | 4/2004 | Walt et al. |
| 6,733,964 B1 | 5/2004 | Chee et al. |
| 6,742,004 B2 | 5/2004 | Sabatini et al. |
| 6,770,441 B2 | 8/2004 | Dickinson et al. |
| 2001/0006630 A1 | 7/2001 | Yacoby-Zeevi |
| 2001/0029049 A1 | 10/2001 | Walt et al. |
| 2001/0041335 A1 | 11/2001 | Goldberg et al. |
| 2001/0053526 A1 | 12/2001 | Lipshutz et al. |
| 2002/0001801 A1 | 1/2002 | Fan et al. |
| 2002/0006617 A1 | 1/2002 | Fan et al. |
| 2002/0009719 A1 | 1/2002 | Walt et al. |
| 2002/0009729 A1 | 1/2002 | McGall et al. |
| 2002/0012913 A1 | 1/2002 | Gunderson et al. |
| 2002/0012925 A1 | 1/2002 | Chee |
| 2002/0012940 A1 | 1/2002 | Lockhart et al. |
| 2002/0022721 A1 | 2/2002 | Trulson et al. |
| 2002/0025520 A1 | 2/2002 | Chee |
| 2002/0028159 A1 | 3/2002 | Lebl et al. |
| 2002/0039728 A1 | 4/2002 | Kain et al. |
| 2002/0044894 A1 | 4/2002 | Lebl et al. |
| 2002/0051971 A1 | 5/2002 | Stuelpnagel et al. |
| 2002/0071339 A1 | 6/2002 | Winkler et al. |
| 2002/0102578 A1 | 8/2002 | Dickinson et al. |
| 2002/0106663 A1 | 8/2002 | Gentalen et al. |
| 2002/0122612 A1 | 9/2002 | Walt et al. |
| 2002/0132221 A1 | 9/2002 | Chee et al. |
| 2002/0132241 A1 | 9/2002 | Fan et al. |
| 2002/0150909 A1 | 10/2002 | Stuepnagel et al. |
| 2002/0172716 A1 | 11/2002 | Walt et al. |
| 2002/0172946 A1 | 11/2002 | Fan et al. |
| 2002/0177141 A1 | 11/2002 | Chee et al. |
| 2002/0187515 A1 | 12/2002 | Chee et al. |
| 2003/0003490 A1 | 1/2003 | Fan et al. |
| 2003/0013114 A1 | 1/2003 | Lipshulz et al. |
| 2003/0016897 A1 | 1/2003 | Walt et al. |
| 2003/0027129 A1 | 2/2003 | Walt et al. |
| 2003/0064364 A1 | 4/2003 | Lockhart et al. |
| 2003/0082566 A1 | 5/2003 | Sylvan |
| 2003/0096239 A1 | 5/2003 | Gunderson et al. |
| 2003/0104434 A1 | 6/2003 | Fan et al. |
| 2003/0108867 A1 | 6/2003 | Chee et al. |
| 2003/0134291 A1 | 7/2003 | Lipshulz et al. |
| 2003/0157504 A1 | 8/2003 | Chee et al. |
| 2003/0165823 A1 | 9/2003 | Cronin et al. |
| 2003/0165830 A1 | 9/2003 | Cronin et al. |
| 2003/0170684 A1 | 9/2003 | Fan |
| 2003/0175773 A1 | 9/2003 | Chee et al. |
| 2003/0207295 A1 | 11/2003 | Gunderson et al. |
| 2003/0211489 A1 | 11/2003 | Shen et al. |
| 2003/0215821 A1 | 11/2003 | Gunderson et al. |
| 2003/0215841 A1 | 11/2003 | Lockhart et al. |
| 2004/0018491 A1 | 1/2004 | Gunderson et al. |
| 2004/0072202 A1 | 4/2004 | McGall et al. |
| 2004/0076987 A1 | 4/2004 | McGall et al. |
| 2004/0114456 A1 | 6/2004 | Winkler et al. |
| 2004/0121364 A1 | 6/2004 | Chee et al. |
| 2004/0137498 A1 | 7/2004 | Fan et al. |
| 2004/0175718 A1 | 9/2004 | Chee et al. |
| 2004/0185482 A1 | 9/2004 | Stuelpnagel et al. |
| 2004/0185483 A1 | 9/2004 | Stuelpnagel et al. |

FOREIGN PATENT DOCUMENTS

| | | |
|---|---|---|
| EP | 0 371 437 | 2/1996 |
| EP | 0 619 321 | 1/1999 |
| EP | 1 090 293 | 12/1999 |
| EP | 1 196 630 | 10/2000 |

| | | |
|---|---|---|
| WO | WO 88/05533 | 7/1988 |
| WO | WO 93/21513 | 10/1993 |
| WO | WO 94/12863 | 6/1994 |
| WO | WO 95/11995 | 5/1995 |
| WO | WO 97/19193 | 5/1997 |
| WO | WO 97/27317 | 7/1997 |
| WO | WO 97/27326 | 7/1997 |
| WO | WO 97/29212 | 8/1997 |
| WO | WO 97/41260 | 11/1997 |
| WO | WO 98/08973 | 3/1998 |
| WO | WO 98/13523 | 4/1998 |
| WO | WO 98/18967 | 5/1998 |
| WO | WO 98/20019 | 5/1998 |
| WO | WO 98/30883 | 7/1998 |
| WO | WO 98/35012 | 8/1998 |
| WO | WO 98/38846 | 9/1998 |
| WO | WO 98/40726 | 9/1998 |
| WO | WO 98/41657 | 9/1998 |
| WO | WO 98/44151 | 10/1998 |
| WO | WO 98/44152 | 10/1998 |
| WO | WO 89/10977 | 11/1998 |
| WO | WO 98/50782 | 11/1998 |
| WO | WO 98/53300 | 11/1998 |
| WO | WO 98/56954 | 12/1998 |
| WO | WO 98/58079 | 12/1998 |
| WO | WO 98/58529 | 12/1998 |
| WO | WO 99/05315 | 2/1999 |
| WO | WO 99/07896 | 2/1999 |
| WO | WO 99/14228 | 3/1999 |
| WO | WO 99/15702 | 4/1999 |
| WO | WO 99/18434 | 4/1999 |
| WO | WO 99/28494 | 6/1999 |
| WO | WO 99/30823 | 6/1999 |
| WO | WO 98/28440 | 7/1999 |
| WO | WO 99/36576 | 7/1999 |
| WO | WO 99/39004 | 8/1999 |
| WO | WO 99/45357 | 9/1999 |
| WO | WO 99/53102 | 10/1999 |
| WO | WO 99/60007 | 11/1999 |
| WO | WO 99/61662 | 12/1999 |
| WO | WO 99/66313 | 12/1999 |
| WO | WO 99/67641 | 12/1999 |
| WO | WO 00/06770 | 2/2000 |
| WO | WO 00/11223 | 3/2000 |
| WO | WO 00/13004 | 3/2000 |
| WO | WO 00/16101 | 3/2000 |
| WO | WO 00/27521 | 5/2000 |
| WO | WO 00/29832 | 5/2000 |
| WO | WO 00/39587 | 7/2000 |
| WO | WO 00/43540 | 7/2000 |
| WO | WO 00/44491 | 8/2000 |
| WO | WO 00/47996 | 8/2000 |
| WO | WO 00/48000 | 8/2000 |
| WO | WO 00/56455 | 9/2000 |
| WO | WO 00/58507 | 10/2000 |
| WO | WO 00/60072 | 10/2000 |
| WO | WO 00/60114 | 10/2000 |
| WO | WO 00/60332 | 10/2000 |
| WO | WO 00/63437 | 10/2000 |
| WO | WO 00/71243 | 11/2000 |
| WO | WO 00/71992 | 11/2000 |
| WO | WO 00/71995 | 11/2000 |
| WO | WO 00/75373 | 12/2000 |
| WO | WO 01/12862 | 2/2001 |
| WO | WO 01/18524 | 3/2001 |
| WO | WO 01/24937 | 4/2001 |
| WO | WO 01/25480 | 4/2001 |
| WO | WO 01/41918 | 6/2001 |
| WO | WO 01/42496 | 6/2001 |
| WO | WO 01/46675 | 6/2001 |
| WO | WO 01/57268 | 8/2001 |
| WO | WO 01/57269 | 8/2001 |
| WO | WO 01/59432 | 8/2001 |
| WO | WO 01/61043 | 8/2001 |
| WO | WO 01/69245 | 9/2001 |
| WO | WO 01/85341 | 11/2001 |
| WO | WO 02/00336 | 1/2002 |
| WO | WO 02/12897 | 2/2002 |
| WO | WO 02/16649 | 2/2002 |
| WO | WO 02/20836 | 3/2002 |
| WO | WO 02/20837 | 3/2002 |
| WO | WO 02/21128 | 3/2002 |
| WO | WO 02/28530 | 4/2002 |
| WO | WO 02/41987 | 5/2002 |
| WO | WO 02/99982 | 12/2002 |

OTHER PUBLICATIONS

Barshop et al., "Luminescent immobilized enzyme test systems for inorgranic pyrophosphate: Assays using firefly luciferase and nicotinamide-monomucleotide adenylyl transferase or adenosine-5'-triphosphate sulfurylase." Analytical Biochemistry 1997: 266-272 (1991).

Brandis et al., "Slow rate of phosphodiester bond formation accounts for the strong bias that Taq DNA polymerase shows against 2', 3'-dideoxynucleotide terminators." Biochemistry 55: 2189-2200 (1990).

Bronk et al., "Combined imaging and chemical sensing using a single optical imaging fiber." Anal. Chem. 67: 2750-2757 (1996).

Burns et al., "An Integrated Nanoliter DNA Analysis Device." Science 282: 484-487 (1998).

Chan and Nie, "Quantum dot bioconjugates for ultrasensitive nonisotopic detection." Scient 281: 2016-2018 (1998).

Chee et al., "Accessing Genetic Information with High-Density DNA Arrays." Science 274(5287).

Chui and Christopoulos, "Hybridization Assays Using an Expressible DNA Fragment Encoding Firefly Luciferase as a label." Anal. Chem. 68: 2304-2308 (1996).

Daubendiek and Kool, "Generation of catalytic RNAs by rolling transcription of synthetic DNA nanocircles." Nature Biotechnology 15: 273-277 (1997).

Dickson et al., "Three-dimensional imaging of single molecules solvated in pores of poly(acrylamide) gels." Science 274(5289): 966 (1996).

Dickson et al., "On/off blinking and switching behaviour of single molecules of green fluorescent protein." Nature 388: 355-358 (1997).

Ferguson et al., "A fiber-optic DNA biosensor microarray for the analysis of gene expression." Nature Biotechnology 14: 1681-1684 (1996).

Fire and Xu, "Rolling replication of short DNA circles." Proc. Natl. Acad. Sci. 92: 4641-4645 (1995).

Ha et al., "Probing the interaction between two single molecules: Fluorescence resonance energy transfer between a single donor and a single acceptor." Proc. Natl. Acad. 93: 6264-6268 (1996).

Hacia, "Resequencing and mutational analysis using oligonucleotide microarrays." Nature Genetics Supplement 21: 42-47 (1999).

Hatch et al., "Rolling circle amplification of DNA immobilized on solid surfaces and its application to multiplex mutation detection." Genetic Analysis: Biomolecular Engineering 15: 35-40 (1999).

Healey and Walt, "Fast Temporal Response Fiber-Optic Chemical Sensors Based on the Photodeposition of Micrometer-scale Polymer Arrays." Anal. Chem. 69: 2213-2216 (1997).

Healey et al., "Photodeposition of Micrometer-Scale Polymer Patterns on Optical Imaging Fibers." Science 269: 1078-1080 (1995).

Hengsakul and Cass, "Protein Patterning with a Photoactivatable Derivative of Biotin." Bioconjugate Chem. 7: 249-254 (1996).

Hyman, "A New Method of Sequencing DNA." Analytical Biochemistry 174: 423-436 (1988).

Ishijima et al., "Simultaneous observation of Individual ATPase and Mechanical Events by a Single Myosin Molecule during Interaction with Actin." Cell 92: 161-171 (1998).

Ito et al., "Fluorescent differential display: arbitrarily primed RT-PCR fingerprinting on an automated DNA sequencer." FEBS 351: 231-236 (1994).

Izawa et al., "Recognition Sites of 3'-OH Group by T7 RNA Polymerase and Its Application to Transcriptional Sequencing." The Journal of Biological Chemistry 273(23): 14242-14246 (1998).

Karamohamed et al., "Production, Purification, and Luminometric Analysis of Recombinant *Saccharomyces cerevisiae* MET3 Adenosine Triphosphate Sulfurylase Expressed in *Escherichia coli*." Protein Expression and Purification 15: 381-388 (1999).

Karamohamed and Nyren, "Real-Time Detection and Quantification of Adenosine Triphosphate Sulfurylase Activity by a Bioluminometric Approach." Analytical Biochemistry 271: 81-85 (1999).

Keller et al., "Single-Molecule Fluorescence Analysis in Solution." Applied Spectroscopy 7(50): 823-958 (1996).

Kievits et al., "NASBA isothermal enzymatic in vitro nucleic acid amplification optimized for the diagnosis of HIV-1 infection." Journal of Virological Methods 35: 273-286 (1991).

Kricka, "Miniaturization of analytical systems." Clinical Chemistry 44(9): 2008-2014 (1998).

Lander, "the New Genomics: Global Views of Biology." Science 274: 536-539 (1996).

Lu et al., "Rolling Circle DNA Synthesis: Small Circular Oligonucleotides as Efficient Templates for DNA Polymerases." J. Am. Chem. Soc. 118:1587-1594 (1996).

Lizardi et al., "Mutation detection and single-molecule counting using isothermal rolling-circle amplification." Nature Genetics 19: 225-232 (1998).

Metzker et al., "Elimination of Residual Natural Nucleotides from 3'-O-Modified-dNTP Syntheses by Enzymatic Mop-Up." BioTechniques 25: 814-817 (1998).

Metzker et al., "Quantitation of Mixed-Base Populations of HIV-1 Variants by Automated DNA Sequencing with BODIPY Dye-Labeled Primers." BioTechniques 25: 446-462 (1998).

Munkholm and Walt, "Polymer Modification of Fiber Optic Chemical Sensors as a Method of Enhancing Fluorescence Signal for pH Measurement." Anal. Chem. 58: 1427-1430 (1986).

Mooney et al., "Patterning of functional antibodies and other proteins by photolithography of silane monolayers." Proc. Natl. Acad. Sci. 93: 12287-12291 (1996).

Narang et al., "Fiber Optic-based biosensor for ricin." Biosensors & Bioelectronics 12(9-10):937-945 (1997).

Nie et al., "Probing Individual Molecules with Confocal Fluorescence Microscopy." Science 266: 1018-1021 (1994).

Nie and Zare, "Optical Detection of Single Molecules." Annu. Rev. Biophys. Biomol. Struct. 26: 567-596 (1997).

Nilsson et al., "Padlock probes reveal single-nucleotide differences, parent of origin and in situ distribution of centromeric sequences in human chromosomes 13 and 21." Nature Genetics 16: 252-255 (1997).

Nilsson et al., "Padlock Probes: Circularizing Oligonucleotides for Localized DNA Detection." Science 265: 2085-2087 (1994).

Nyren, "Apyrase Immobilized on Paramagnetic Beads Used to Improve Detection Limits in Bioluminometric ATP Monitoring." J. Biolumin. Chemilumin.

Nyren et al., "Detection of Single-Base Changes Using a Bioluminometric Primer Extension Assay."Analytical Biochemistry 244: 367-373 (1997).

Nyren et al., "Solid Phase DNA Minisequencing by an Enzymatic Luminometric Inorganic Pyrophosphate Detection Assay." Analytical Biochemistry 208: 171-175 (1993).

Oker-Blom et al., "A Baculovirus-Expressed Fusion Protein Containing the Antibody-Binding Doman of Protein A and Insect Luciferase." BioTechniques 14(5): 800-807 (1993).

Parthasarathy and Martin, "Synthesis of polymeric microcapsule arrays and their use for enzyme immobilization." Nature 369: 298-301 (1994).

Pierce et al., "Imaging individual green fluorescent proteins." Scientific Correspondence.

Pirrung and Huang, "A General method for the Spatially Defined Immobilization of Biomolecules on Glass Surfaces Using "Caged" Biotin." Bioconjugate Chem. 7: 317-321 (1996).

Rawlinson et al., "Analysis of the Complete DNA Sequence of Murine Cytomegalovirus." Journal of Virology 8833-8849 (1996).

Ribeiro et al., "Immobilization of Luciferase from a Firefly Lantern Extract on Glass Strips as an Alternative Strategy for Luminescent Detection of ATP," J. Biolumin Chemilumin 13: 371-378 (1998).

Ronaghi et al., "Real-Time DNA Sequencing Using Detection of Pyrophosphate Release." Analytical Biochemistry 242: 84-89 (1996).

Ronaghi et al., "A Sequencing Method Based on Real-Time Pyrophosphate." Science 281: 363. 365 (1998).

Ronaghi et al., "Analyses of Secondary Structures on DNA by Pyrosequencing." Analytical Biochemistry 267: 65-71 (1999).

Ronaghi, "Pryosequencing: A Tool for Sequence-Based DNA Analysis." Royal Institute of Technology Department of Technology.

Service, "Microchip Arrays Put DNA on the Spot." Science 282(5388).

Venter et al., "Shotgun Sequencing of the Human Genome." Science 280(5369): 1540.

Walker et al., "Strand displacement amplification—an isothermal, in vitro DNA amplification technique." Nucleic Acids Research 20(7): 1691-1696 (1992).

Walker et al., "Isothermal in vitro amplification of DNA by a restriction enzyme/DNA polymerase system." Proc. Natl. Acad. 89: 392-396 (1992).

Wang et al., "Specific Immobilization of Firefly Luciferase through a Biotin Carboxyl Carrier Protein Domain." Analytical Biochemistry 246: 133-139 (1997).

Wang et al., "Large-Scale Identification, Mapping, and Genotyping of Single-Nucleotide Polymorphisms in the Human Genome." Science 280: 1077-1082 (1998).

Wang et al., "Force and Velocity Measured for single Molecules of RNA Polymerase." Science 282: 902-907 (1998).

Weisiger, "Impact of Extracellular Diffusion on Hepatic Uptake Kinetics." ASTRACT: 1-26.

Wooster et al., "Localization of a Breast Cancer Susceptibility Gene, BRCA2, to Chromosome 13q12-13." Science 265: 277-285 (1994).

Xie and Lu, "Single-molecule Enzymology." The Journal of Biological Chemistry 274(23): 15967-15970 (1999).

Yin et al., "Transcription Against an Applied Force." Science 270:1653-1657.

Nyren, "Enzymatic Method for Continuous Monitoring of DNA Polymerase Activity." Analytical Biochemistry 167: 235-238 (1987).

International Search Report for PCT/US00/25290, mailed Nov. 28, 2001.

Hoheisel, J.D. "Oligomer-chip Technology." Trends in Biotechnology 15:465-469 (1997).

International Preliminary Examination Report for PCT/US02/08700.

Mira and Church (1999). *Nuc. Acids Res.* 27(e34): i-vi.

Tawfik and Griffiths (1998). *Nature Biotechnol. 16*: 652-656.

International Search Report for PCT/US02/08700, mailed Jul. 12, 2002.

Pantano et al. "Ordered Nanowell Arrays" Chemistry of Materials, 8: 2832-2835.

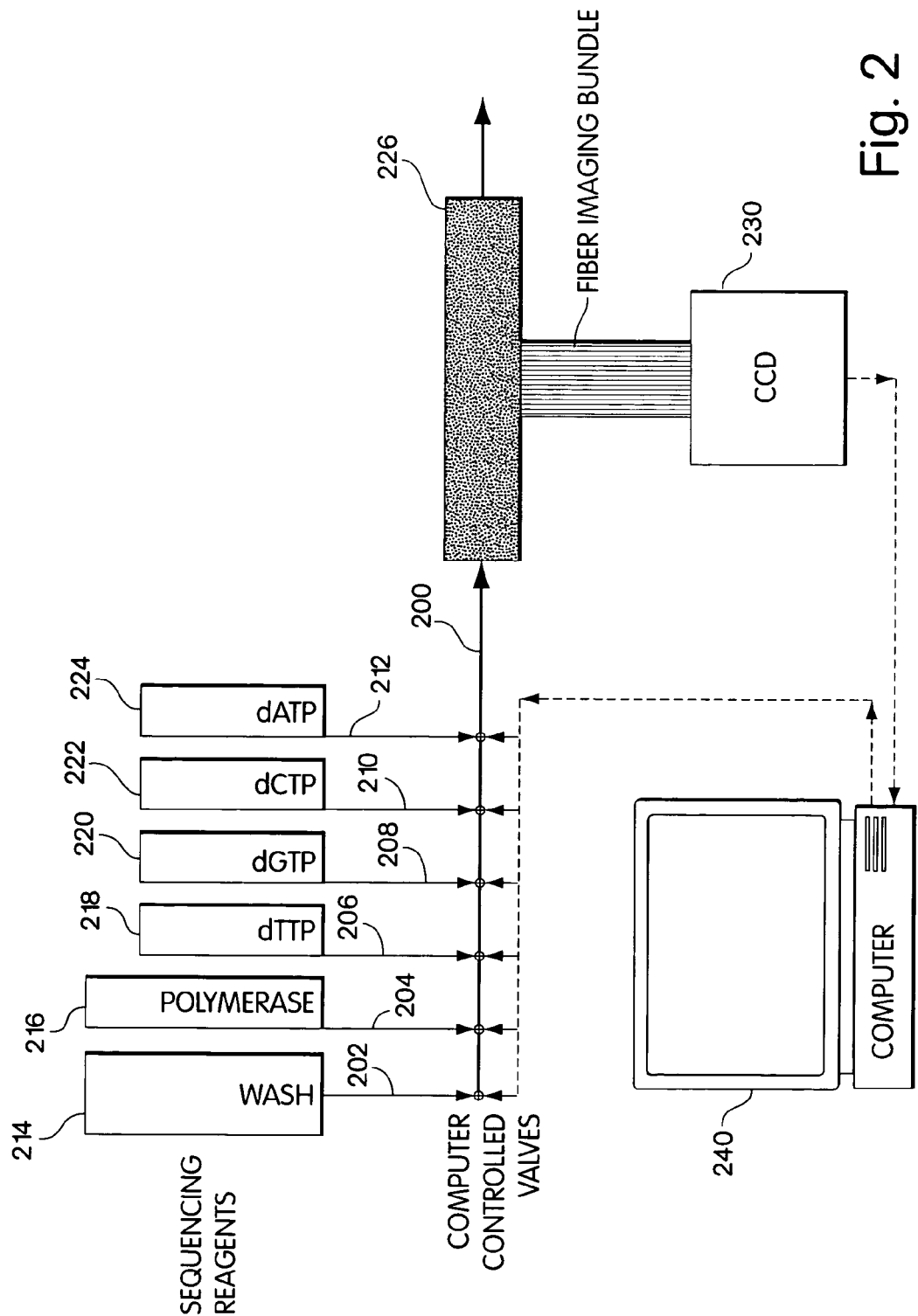

METHOD OF SEQUENCING A NUCLEIC ACID

RELATED APPLICATIONS

This application claims priority to U.S. Ser. No. 09/664,197 filed Sep. 18, 2000, which claims priority to U.S. Ser. No. 09/398,833, filed Sep. 16, 1999. The contents of these applications are incorporated herein by reference in their entireties.

FIELD OF THE INVENTION

The invention relates to methods and apparatuses for determining the sequence of a nucleic acid.

BACKGROUND OF THE INVENTION

Many diseases are associated with particular DNA sequences. The DNA sequences are often referred to as DNA sequence polymorphisms to indicate that the DNA sequence associated with a diseased state differs from the corresponding DNA sequence in non-afflicted individuals. DNA sequence polymorphisms can include, e.g., insertions, deletions, or substitutions of nucleotides in one sequence relative to a second sequence. An example of a particular DNA sequence polymorphism is 5'-ATCG-3', relative to the sequence 5'-ATGG-3' at a particular location in the human genome. The first nucleotide 'G' in the latter sequence has been replaced by the nucleotide 'C' in the former sequence. The former sequence is associated with a particular disease state, whereas the latter sequence is found in individuals not suffering from the disease. Thus, the presence of the nucleotide sequence '5-ATCG-3' indicates the individual has the particular disease. This particular type of sequence polymorphism is known as a single-nucleotide polymorphism, or SNP, because the sequence difference is due to a change in one nucleotide.

Techniques which enable the rapid detection of as little as a single DNA base change are therefore important methodologies for use in genetic analysis. Because the size of the human genome is large, on the order of 3 billion base pairs, techniques for identifying polymorphisms must be sensitive enough to specifically identify the sequence containing the polymorphism in a potentially large population of nucleic acids.

Typically a DNA sequence polymorphism analysis is performed by isolating DNA from an individual, manipulating the isolated DNA, e.g., by digesting the DNA with restriction enzymes and/or amplifying a subset of sequences in the isolated DNA. The manipulated DNA is then examined further to determine if a particular sequence is present.

Commonly used procedures for analyzing the DNA include electrophoresis. Common applications of electrophoresis include agarose or polyacrylamide gel electrophoresis. DNA sequences are inserted, or loaded, on the gels and subjected to an electric field. Because DNA carries a uniform negative charge, DNA will migrate through the gel based on properties including sequence length, three-dimensional conformation and interactions with the gel matrix ratio upon application of the electrical field. In most applications, smaller DNA molecules will migrate more rapidly through the gel than larger fragments. After electrophoresis has been continued for a sufficient length of time, the DNA molecules in the initial population of DNA sequences will have been separated according to their relative sizes.

Particular DNA molecules can then be detected using a variety of detection methodologies. For some applications, particular DNA sequences are identified by the presence of detectable tags, such as radioactive labels, attached to specific DNA molecules.

Electrophoretic-based separation analyses can be less desirable for applications in which it is desirable to rapidly, economically, and accurately analyze a large number of nucleic acid samples for particular sequence polymorphisms. For example, electrophoretic-based analysis can require a large amount of input DNA. In addition, processing the large number of samples required for electrophoretic-based nucleic acid based analyses can be labor intensive. Furthermore, these techniques can require samples of identical DNA molecules, which must be created prior to electrophoresis at costs that can be considerable.

Recently, automated electrophoresis systems have become available. However, electrophoresis can be ill-suited for applications such as clinical sequencing, where relatively cost-effective units with high throughput are needed. Thus, the need for non-electrophoretic methods for sequencing is great. For many applications, electrophoreses is used in conjunction with DNA sequence analysis.

Several alternatives to electrophoretic-based sequencing have been described. These include scanning tunnel electron microscopy, sequencing by hybridization, and single molecule detection methods.

Another alternative to electrophoretic-based separation is analysis is solid substrate-based nucleic acid analyses. These methods typically rely upon the use of large numbers of nucleic acid probes affixed to different locations on a solid support. These solid supports can include, e.g., glass surfaces, plastic microtiter plates, plastic sheets, thin polymers, or semi-conductors. The probes can be, e.g., adsorbed or covalently attached to the support, or can be microencapsulated or otherwise entrapped within a substrate membrane or film.

Substrate-based nucleic acid analyses can include applying a sample nucleic acid known or suspected of containing a particular sequence polymorphism to an array of probes attached to the solid substrate. The nucleic acids in the population are allowed to hybridize to complementary sequences attached to the substrate, if present. Hybridizing nucleic acid sequences are then detected in a detection step.

Solid support matrix-based hybridization and sequencing methodologies can require a high sample-DNA concentration and can be hampered by the relatively slow hybridization kinetics of nucleic acid samples with immobilized oligonucleotide probes. Often, only a small amount of template DNA is available, and it can be desirable to have high concentrations of the target nucleic acid sequence. Thus, substrate based detection analyses often include a step in which copies of the target nucleic acid, or a subset of sequences in the target nucleic acid, is amplified. Methods based on the Polymerase Chain Reaction (PCR), e.g., can increase a small number of probes targets by several orders of magnitude in solution. However, PCR can be difficult to incorporate into a solid-phase approach because the amplified DNA is not immobilized onto the surface of the solid support matrix.

Solid-phase based detection of sequence polymorphisms has been described. An example is a "mini-sequencing" protocol based upon a solid phase principle described by Hultman, et al., 1988. *Nucl. Acid Res.* 17: 4937–4946; Syvanen, et al., 1990. *Genomics* 8: 684–692). In this study, the incorporation of a radiolabeled nucleotide was measured and used for analysis of a three-allelic polymorphism of the human apolipoprotein E gene. However, such radioactive methods are not well-suited for routine clinical applications, and hence the development of a simple, highly sensitive non-radioactive method for rapid DNA sequence analysis has also been of great interest.

SUMMARY OF THE INVENTION

The invention is based in part on the discovery of a highly sensitive method for determining the sequences of nucleic acids attached to solid substrates, and of novel substrate services for analyzing nucleic acid sequences.

Accordingly, in one aspect, the invention includes a substrate for analyzing a nucleic acid. The substrate includes a fiber optic surface onto which has been affixed one or more nucleic acid sequences. The fiber optic surface can be cavitated, e.g., a hemispherical etching of the opening of a fiber optic. The substrate can in addition include a plurality of bundled fiber optic surfaces, where one or more of the surfaces have anchored primers.

In another aspect, the invention includes an apparatus for analyzing a nucleic acid sequence. The apparatus can include a reagent delivery chamber, e.g., a perfusion chamber, wherein the chamber includes a nucleic acid substrate, a conduit in communication with the perfusion chamber, an imaging system, e.g., a fiber optic system, in communication with the perfusion chamber; and a data collection system in communication with the imaging system. The substrate can be a planar substrate. In other embodiments, the substrate can be the aforementioned fiber optic surface having nucleic acid sequences affixed to its termini.

In a further aspect, the invention includes a method for sequencing a nucleic acid. The method include providing a primed anchor primer circular template complex and combining the complex with a polymerase, and nucleotides to generate concatenated, linear complementary copies of the circular template. The extended anchor primer-circular template complex can be generated in solution and then linked to a solid substrate. Alternatively, one or more or more nucleic acid anchor primers can be linked to a solid support and then annealed to a plurality of circular nucleic acid templates. The linked nucleic acid anchor primer is then annealed to a single-stranded circular template to yield a primed anchor primer-circular template complex.

A sequencing primer is annealed to the circular nucleic acid template to yield a primed sequencing primer-circular nucleic acid template complex. Annealing of the sequencing primer can occur prior to, or after, attachment of the extended anchor primer to the solid substrate. The sequence primer is the extended with a polymerase and a predetermined nucleotide triphosphate to yield a sequencing product and a sequencing reaction byproduct, e.g., inorganic pyrophosphate. If the predetermined nucleotide is incorporated into the primer, the sequencing reaction byproduct is generated and then identified, thereby determining the sequence of the nucleic acid. If the predetermined nucleotide is incorporated in the sequencing primer multiple times, e.g., the concatenated nucleic acid template has multiple identical nucleotides, the quantity or concentration of sequencing reaction byproduct is measured to determine the number of nucleotides incorporated. If desired, additional predetermined nucleotide triphosphates can be added, e.g., sequentially, and the presence or absence of sequence byproducts associated with each reaction can be determined.

In a still further aspect, the invention includes a method for sequencing a nucleic acid by providing one or more nucleic acid anchor primers linked to a plurality of anchor primers linked to a fiber optic surface substrate, e.g., the solid substrate discussed above.

In various embodiments of the apparatuses and methods described herein, the solid substrate includes two or more anchoring primers separated by approximately 10 μm to approximately 200 μm, 50 μm to approximately 150 μm, 100 μm to approximately 150 μm, or 150 μm. The solid support matrix can include a plurality of pads that are covalently linked to the solid support. The surface area of the pads can be, e.g., 10 μm$^2$ and one or more pads can be separated from one another by a distance ranging from approximately 50 μm to approximately 150 μm.

In preferred embodiments, at least a portion of the circular nucleic acid template is single-stranded DNA. The circular nucleic acid template can be, e.g., genomic DNA or RNA, or a cDNA copy thereof. The circular nucleic acid can be, e.g., 10–10,000 or 10–1000, 10–200, 10–100, 10–50, or 20–40 nucleotides in length.

In some embodiments, multiple copies of one or more circular nucleic acids in the population are generated by a polymerase chain reaction. In other embodiments, the primed circular template is extended by rolling circle amplification (RCA) to yield a single-stranded concatamer of the annealed circular nucleic acid template. If desired, the template amplified by rolling circle amplification and be further amplified by annealing a reverse primer to the single-stranded concatamer to yield a primed concatamer template and combining the primed concatamer template with a polymerase enzyme to generate multiple copies of the concatamer template. In still further embodiments, the template can be extended by a combination of PCR and RCA-amplification.

In preferred embodiments, the sequencing byproduct analyzed is pyrophosphate. When pyrophosphate is used as the detected byproduct, a preferred nucleotide triphosphate for use by the polymerase in extending the primed sequencing primer is a dATP analog, e.g., α-thio ATP.

Preferably, the pyrophosphate is detected by contacting the sequencing byproduct with ATP sulfurylase under conditions sufficient to form ATP. The ATP can then be detected, e.g., with an enzyme which generates a detectable product upon reaction with ATP. A preferred enzyme for detecting the ATP is luciferase. If desired, a wash buffer, can be used between addition of various reactants herein. Preferably, apyrase is used to remove, e.g., unreacted dNTP used to extend the sequencing primer. The wash buffer can optionally include apyrase.

The reactants and enzymes used herein, e.g., the ATP sulfurylase, luciferase, and apyrase, can be attached to the solid surface.

The anchor primer sequence can include, e.g. a biotin group, which can link the anchor primer to the solid support via an avidin group attached to the solid support. In some embodiments, the anchor primer is conjugated to a biotin-bovine serum albumin (BSA) moiety. The biotin-BSA moiety can be linked to an avidin-biotin group on the solid support. If desired, the biotin-BSA moiety on the anchor primer can be linked to a BSA group on the solid support in the presence of silane.

In some embodiments, the solid support includes at least one optical fiber.

The invention also provides a method for profiling the concentrations of mRNA transcripts present in a cell. The identity of a transcript may be determined by the sequence at its 3' terminus (additional fragments may be used to distinguish between splice variants with identical 3' sequence). A sequencing apparatus having 10,000 sites could, in a single run, determine the mRNA species present at a concentration of 1:10,000 or higher. Multiple runs, or multiple devices, could readily extend the limit to 1:100,000 or 1:1,000,000. This performance would be superior to current technologies, such as microarray hybridization, which have detection limits in the range 1:10,000 to 1:100,000.

In a further embodiment, the sequence of the amplified nucleic acid can be determined using by products of RNA synthesis. In this embodiment, an RNA transcript is generated from a promoter sequence present in the circular nucleic acid template library. Suitable promoter sites and their cognate RNA polymerases include RNA polymerases from $E.$ $coli$, the RNA polymerase from the bacteriophage $T_3$, the RNA polymerase from the bacteriophage $T_7$, the RNA polymerase from the bacteriophage SP6, and the RNA polymerases from the viral families of bromoviruses, tobamoviruses, tombusvirus, lentiviruses, hepatitis C-like viruses, and picornaviruses. To determine the sequence of an RNA transcript, a predetermined NTP, i.e., an ATP, CTP, GTP, or UTP, is incubated with the template in the presence of the RNA polymerase. Incorporation of the test NTP into a nascent RNA strand can be determined by assaying for the presence of PPi using the enzymatic detection discussed herein.

The disclosures of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. Unless expressly stated otherwise, the techniques employed or contemplated herein are standard methodologies well known to one of ordinary skill in the art. The examples of embodiments are for illustration purposes only. All patents and publications cited in this specification are incorporated by reference.

BRIEF DESCRIPTION OF THE DRAWINGS

FIG. 2 is a drawing of a sequencing apparatus according to the present invention.

DETAILED DESCRIPTION OF THE INVENTION

Figure 1A:
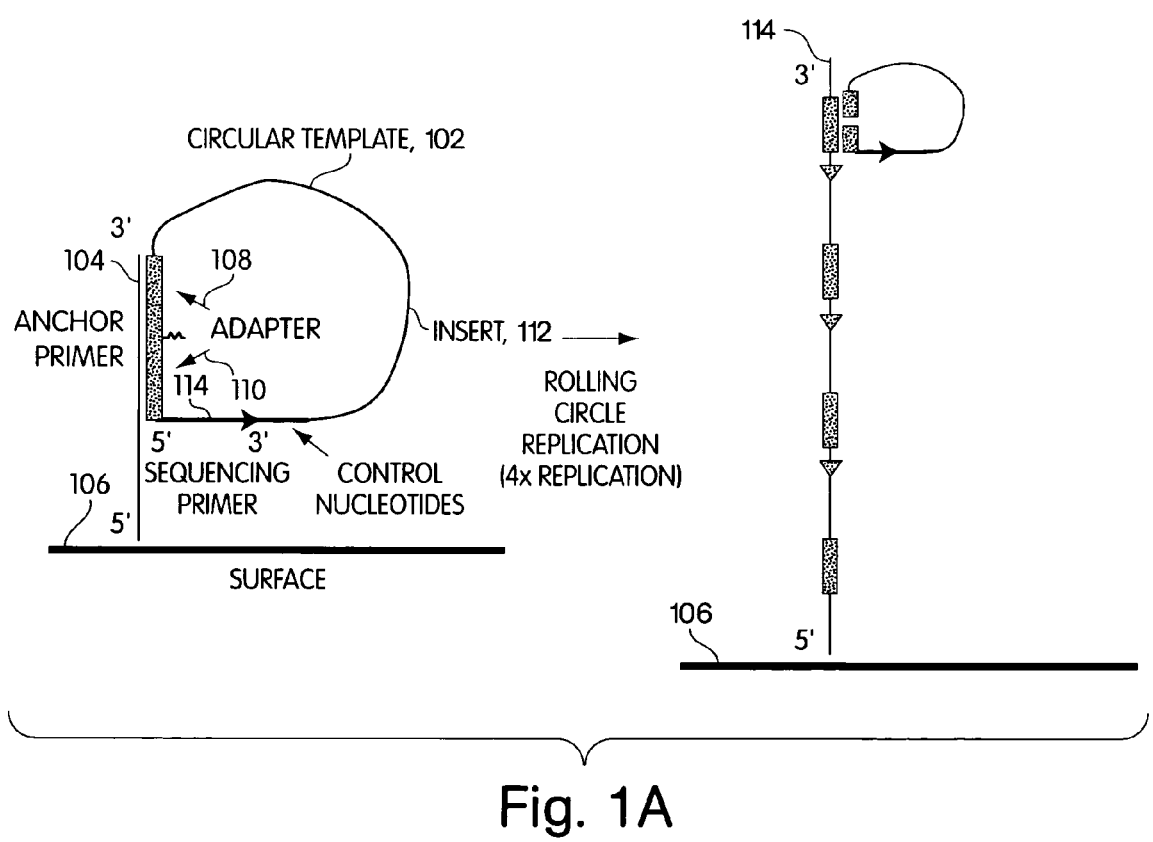
FIGS. 1A–D are schematic illustrations of rolling circle based amplification using an anchor primer.

The invention provides methods of preparing nucleic acid sequences for subsequent analysis, e.g., sequencing, as well as methods and apparatuses for sequencing nucleic acids.

The methods described herein include a sample preparation process that results in a solid substrate array containing a plurality of anchor primers covalently linked to a nucleic acid containing one or more copies complementary to a target nucleic acid. Formation of the covalently linked anchor primer and one or more copies of the target nucleic acid preferably occurs by annealing the anchor primer to a complementary region of a circular nucleic acid, and then extending the annealed anchor primer with a polymerase to result in formation of a nucleic acid containing one or more copies of a sequence complementary to the circular nucleic acid.

Attachment of the anchor primer to the solid substrate can occur before, during, or subsequent to extension of the annealed anchor primer. Thus, in one embodiment, one or more anchor primers are linked to the solid substrate, after which the anchor primer is annealed to a target-nucleic acid and extended in the presence of a polymerase. Alternatively, in a second embodiment, an anchor primers is first annealed to a target nucleic acid, and a 3'OH terminus of the annealed anchor primer is extended with a polymerase. The extended anchor primer is then linked to the solid substrate. By varying the sequence of anchor primers, it is possible to specifically amplify distinct target nucleic acids present in a population of nucleic acids.

Sequences in the target nucleic acid can be identified in a number of ways. Preferably, a sequencing primer is annealed to the amplified nucleic acid and used to generate a sequencing product. The nucleotide sequence of the sequence product is then determined, thereby allowing for the determination of the nucleic acid.

The methods and apparatuses described herein allow for the determination of nucleic acid sequence information without the need for first cloning a nucleic acid. In addition, the method is highly sensitive and can be used to determine the nucleotide sequence of a template nucleic acid which is present in only a few copies in a starting population of nucleic acids.

The methods and apparatuses described are generally useful for any application in which the identification of any particular nucleic acid sequence is desired. For example, the methods allow for identification of single nucleotide polymorphisms (SNPs), haplotypes involving multiple SNPs or other polymorphisms on a single chromosome, and transcript profiling. Other uses include sequencing of artificial DNA constructs to confirm or elicit their primary sequence, or to isolate specific mutant clones from random mutagenesis screens, as well as to obtain the sequence of cDNA from single cells, whole tissues or organisms from any developmental stage or environmental circumstance in order to determine the gene expression profile from that specimen. In addition, the methods allow for the sequencing of PCR products and/or cloned DNA fragments of any size isolated from any source.

The methods of the present invention can be also used for the sequencing of DNA fragments generated by analytical techniques that probe higher order DNA structure by their differential sensitivity to enzymes, radiation or chemical treatment (e.g., partial DNase treatment of chromatin), or for the determination of the methylation status of DNA by comparing sequence generated from a given tissue with or without prior treatment with chemicals that convert methylcytosine to thymine (or other nucleotide) as the effective base recognized by the polymerase. Further, the methods of the present invention can be used to assay cellular physiology changes occurring during development or senescence at the level of primary sequence.

Methods of Sequencing Nucleic Acids

Structure of Anchor Primers

Anchor primers in general include a stalk region and at least two contiguous adapter regions. The stalk region is present at the 5' end of the anchor primer and includes a region of nucleotides for attaching the anchor primer to the solid substrate.

The anchor primer in general includes a region which hybridizes to a complementary sequence present in one or more members of a population of nucleic acid sequences. In some embodiments, the anchor primer includes two adjoining regions which hybridize to complementary regions ligated to separate ends of a target nucleic acid sequence. This embodiment is illustrated in FIG. 1, which is discussed in more detail below.

In some embodiments, the adapter regions in the anchor primers are complementary to non-contiguous regions of sequence present in a second nucleic acid sequence. Each adapter region, for example, can be homologous to each terminus of a fragment produced by digestion with one or more restriction endonucleases. The fragment can include, e.g., a sequence known or suspected to contain a sequence polymorphism.

In another example, the anchor primer may contain two adapter regions that are homologous to a gapped, i.e., non-contiguous because of a deletion of one or more nucleotides, region of a target nucleic acid sequence. When adapter regions having these sequences are used, an aligning oligonucleotide corresponding to the gapped sequence may be annealed to the anchor primer along with a population of template nucleic acid molecules.

The anchor primer may optionally contain additional elements, e.g., one or more restriction enzyme recognition sites, RNA polymerase binding sites (e.g., a T7 promoter site).

One or more of the adapter regions may include, e.g., a restriction enzyme recognition site or sequences present in identified DNA sequences, e.g., sequences present in known genes. One or more adapter regions may also include sequences known to flank sequence polymorphisms. Sequence polymorphisms include nucleotide substitutions, insertions, deletions, or other rearrangements which result in a sequence difference between two otherwise identical nucleic acid sequences. An example of a sequence polymorphism is a single nucleotide polymorphism (SNP).

Linking of Anchor Primers to a Solid Support

In general, any nucleic acid capable of base-pairing can be used as an anchor primer. In some embodiments, the anchor primer is an oligonucleotide. As utilized herein the term oligonucleotide includes linear oligomers of natural or modified monomers or linkages, e.g., deoxyribonucleosides, ribonucleosides, anomeric forms thereof, peptide nucleic acids (PNAs), and the like, that are capable of specifically binding to a target polynucleotide by way of a regular pattern of monomer-to-monomer interactions. These types of interactions can include, e.g., Watson-Crick type of base-pairing, base stacking, Hoogsteen or reverse-Hoogsteen types of base-pairing, or the like. Generally, the monomers are linked by phosphodiester bonds, or analogs thereof, to form oligonucleotides ranging in size from, e.g., 3–200, 8–150, 10–100, 20–80, or 25–50 monomeric units. Whenever an oligonucleotide is represented by a sequence of letters, it is understood that the nucleotides are oriented in the 5'→3' direction, from left-to-right, and that the letter "A" donates deoxyadenosine, the letter "T" denotes thymidine, the letter "C" denotes deoxycytosine, and the letter "G" denotes deoxyguanosine, unless otherwise noted herein. The oligonucleotides of the present invention can include non-natural nucleotide analogs. However, where, for example, processing by enzymes is required, or the like, oligonucleotides comprising naturally-occurring nucleotides are generally required for maintenance of biological function.

Any material can be used as the solid support material, as long as the surface allows for stable attachment of the primers and detection of nucleic acid sequences. The solid support material can be planar or can be cavitated. e.g., in a cavitated terminus of a fiber optic. In some embodiments, the solid support is optically transparent, e.g., glass.

The anchor primer can be linked to the solid support to reside on or within the solid support. In some embodiments, the plurality of anchor primers is linked to the solid support so they are spaced at regular intervals within an array. The periodicity between primers is preferably greater than either than the root-mean-square distance that products of the sequencing reactions diffuse prior to detection or the optical resolving power of the detection system, both of which are described in more detail below. The distance between primers on a solid substrate can be, e.g., 10–400 μm, 50–150 μm, 100–1 50 μm, or 150 μm.

An array of attachment sites on the optically transparent solid support can be constructed using lithographic techniques commonly used in the construction of electronic integrated circuits as described in, e.g., techniques for attachment described in U.S. Pat. Nos. 5,5143,854, 5,445, 934, 5,744,305, and 5,800,992; Chee et al., Science 274: 610–614 (1996); Fodor et al., Nature 364: 555–556 (1993); Fodor et al., Science 251: 767–773 (1991); Gushin, et al., Anal. Biochem. 250: 203–211 (1997); Kinosita et al., Cell 93: 21–24 (1998); Kato-Yamada et al., J. Biol. Chem. 273: 19375–19377 (1998); and Yasuda et al., Cell 93: 1117–1124 (1998). Photolithography and electron beam lithography sensitize the solid support or substrate with a linking group that allows attachment of a modified biomolecule (e.g., proteins or nucleic acids). See e.g., Service, Science 283: 27–28 (1999); Rai-Choudhury, HANDBOOK OF MICROLITHOGRAPHY, MICROMACHINING, AND MICROFABRICATION, VOLUME I: MICROLITHOGRAPHY, Volume PM39, SPIE Press (1997). Alternatively, an array of sensitized sites can be generated using thin-film technology as described in Zasadzinski et al., Science 263: 1726–1733 (1994). The contents of all of these patents and publications are incorporated by reference in their entirety.

Anchor primers are linked to the solid substrate at the sensitized sites. A region of a solid substrate containing a linked primer is an anchor pad. Thus, by specifying the sensitized states on the solid support, it is possible to form an array or matrix of anchored pads. The anchor pads can be, e.g., small diameter spots etched at evenly spaced intervals on the solid support.

The anchor primer can be attached to the solid support via a covalent or non-covalent interaction. In general, any linkage recognized in the art can be used. Examples of such linkages common in the art include any suitable metal (e.g., $Co^{2+}$, $Ni^{2+}$)-hexahistidine complex, a biotin binding protein, e.g., NEUTRAVIDIN™ modified avidin (Pierce Chemicals, Rockford, Ill.), streptavidin/biotin, avidin/biotin, glutathione S-transferase (GST)/glutathione, monoclonal antibody/antigen, and maltose binding protein/maltose, and pluronic coupling technologies. Samples containing the appropriate tag are incubated with the sensitized substrate so that zero, one, or multiple molecules attach at each sensitized site.

One biotin-(strept-)avidin-based anchoring method uses a thin layer of a photoactivatable biotin analog dried onto a solid surface. (Hengsakul and Cass, 1996. *Biocongjugate*

Chem. 7: 249–254). The biotin analog is then exposed to white light through a mask, so as to create defined areas of activated biotin. Avidin (or streptavidin) is then added and allowed to bind to the activated biotin. The avidin possesses free biotin binding sites which can be utilized to "anchor" the biotinylated oligonucleotides through a biotin-(strept-) avidin linkage.

Alternatively, the anchor primer can be attached to the solid support with a biotin derivative possessing a photo-removable protecting group. This moiety is covalently bound to bovine serum albumin (BSA), which is attached to the solid support, e.g., a glass surface. See Pirrung and Huang, 1996. *Bioconjugate Chem.* 7: 317–321. A mask is then used to create activated biotin within the defined irradiated areas. Avidin may then be localized to the irradiated area, with biotinylated DNA subsequently attached through a BSA-biotin-avidin-biotin link. If desired, an intermediate layer of silane is deposited in a self-assembled monolayer on a silicon dioxide silane surface that can be patterned to localize BSA binding in defined regions. See e.g., Mooney, et al., 1996. *Proc. Natl. Acad. Sci. USA* 93: 12287–12291.

In pluorinic based attachment, the anchor primers are first attached to the termini of a polyethylene oxide-polypropylene oxide-polyethylene oxide triblock copolymer, which is also known as a pluronic compound. The pluronic moiety can be used to attach the anchor primers to a solid substrate.

Pluronics attach to hydrophobic surfaces by virtue of the reaction between the hydrophobic surface and the polypropylene oxide. The remaining polyethylene oxide groups extend off the surface, thereby creating a hydrophilic environment. Nitrilotriacetic acid (NTA) can be conjugated to the terminal ends of the polyethylene oxide chains to allow for hexahistidine tagged anchor primers to be attached. In another embodiment, pyridyl disulfide (PDS) can be conjugated to the ends of the polyethylene chains allowing for attachment of a thiolated anchor primer via a disulfide bond. In one preferred embodiment, Pluronic F108 (BASF Corp.) is used for the attachment.

Each sensitized site on a solid support is potentially capable of attaching multiple anchor primers. Thus, each anchor pad may include one or more anchor primers. It is preferable to maximize the number of pads that have only a single productive reaction center (e.g., the number of pads that, after the extension reaction, have only a single sequence extended from the anchor primer). This can be accomplished by techniques which include, but are not limited to: (i) varying the dilution of biotinylated anchor primers that are washed over the surface; (ii) varying the incubation time that the biotinylated primers are in contact with the avidin surface; or (iii) varying the concentration of open- or closed-circular template so that, on average, only one primer on each pad is extended to generate the sequencing template.

In some embodiments, each individual pad contains just one linked anchor primer. Pads having only one anchor primer can be made by performing limiting dilutions of a selected anchor primer on to the solid support such that, on average, only one anchor primer is deposited on each pad. The concentration of anchor primer to be applied to a pad can be calculated utilizing, for example, a Poisson distribution model.

In order to maximize the number of reaction pads that contain a single anchor primer, a series of dilution experiments are performed in which a range of anchor primer concentrations or circular template concentrations are varied. For highly dilute concentrations of primers, primers and circular templates binding to the same pad will be independent of each other, and a Poisson distribution will characterize the number of anchor primers extended on any one pad. Although there will be variability in the number of primers that are actually extended, a maximum of 37% of the pads will have a single extended anchor primer (the number of pads with a single anchor oligonucleotide). This number can be obtained as follows.

Let $N_p$ be the average number of anchor primers on a pad and f be the probability that an anchor primer is extended with a circular template. Then the average number of extended anchor primers per pad is $N_p f$, which is defined as the quantity a. There will be variability in the number of primers that are actually extended. In the low-concentration limit, primers and circular templates binding to the same pad will be independent of each other, and a Poisson distribution P(n) will characterize the number of anchor primers n extended on any pad. This distribution may be mathematically defined by: $P(n)=(a^n/n!)\exp(-a)$, with $P(1)=a \exp(-a)$. The probability P(1) assumes it maximum value $\exp(-1)$ for a=1, with 37% of pads having a single extended anchor primer.

A range of anchor primer concentrations and circular template concentrations may be subsequently scanned to find a value of $N_p f$ closest to 1. A preferable method to optimize this distribution is to allow multiple anchor primers on each reaction pad, but use a limiting dilution of circular template so that, on average, only one primer on each pad is extended to generate the sequencing template.

Alternatively, at low concentrations of anchor primers, at most one anchor primer will likely be bound on each reaction pad. A high concentration of circular template may be used so that each primer is likely to be extended.

Where the reaction pads are arrayed on a planar surface or a fiber optic array (FORA), the individual pads are approximately 10 μm on a side, with a 100 μm spacing between adjacent pads. Hence, on a 1 cm surface a total of approximately 10,000 microreactors could be deposited, and, according to the Poisson distribution, approximately 3700 of these will contain a single anchor primer. In certain embodiments, after the primer oligonucleotide has been attached to the solid support, modified, e.g., biotinylated, enzymes are deposited to bind to the remaining, unused avidin binding sites on the surface.

In other embodiments multiple anchor primers are attached to any one individual pad in an array. Limiting dilutions of a plurality of circular nucleic acid templates (described in more detail below) may be hybridized to the anchor primers so immobilized such that, on average, only one primer on each pad is hybridized to a nucleic acid template. Library concentrations to be used may be calculated utilizing, for example, limiting dilutions and a Poisson distribution model.

Libraries of Single-Stranded Circular Templates

A plurality of nucleic acid templates, e.g., a nucleic acid library, in general includes open circular or closed circular nucleic acid molecules. A "closed circle" is a covalently closed circular nucleic acid molecule, e.g., a circular DNA or RNA molecule. An "open circle" is a linear single-stranded nucleic acid molecule having a 5' phosphate group and a 3' hydroxyl group. In some embodiments, the open circle is formed in situ from a linear double-stranded nucleic acid molecule. The ends of a given open circle nucleic acid molecule can be ligated by DNA ligase. Sequences at the 5' and 3' ends of the open circle molecule are complementary to two regions of adjacent nucleotides in a second nucleic acid molecule, e.g., an adapter region of an anchor primer, or to two regions that are nearly adjoining in a second DNA molecule. Thus, the ends of the open-circle molecule can be ligated using DNA ligase, or extended by DNA polymerase in a gap-filling reaction. Open circles are described in detail in Lizardi, U.S. Pat. No. 5,854,033. An open circle can be converted to a closed circle in the presence of a DNA ligase (for DNA) or RNA ligase following, e.g., annealing of the open circle to an anchor primer.

If desired, nucleic acid templates can be provided as padlock probes. Padlock probes are linear oligonucleotides that include target-complementary sequences located at each end, and which are separated by a linker sequence. The linkers can be ligated to ends of members of a library of nucleic acid sequences that have been, e.g., physically sheared or digested with restriction endonucleases. Upon hybridization to a target-sequence, the two ends of the probes are brought in juxtaposition, and they can then be joined through enzymatic ligation. The linkers can be ligated to ends of members of a library of nucleic acid sequences that have been, e.g., physically sheared or digested with restriction endonucleases.

The 5'- and 3'-terminal regions of these linear oligonucleotides are designed to basepair adjacent to one another on a specific target sequence strand, thus the termini of the linear oligonucleotide are brought into juxtaposition by hybridization to the target sequence. This juxtaposition allows the two probe segments (if properly hybridized) to be covalently-bound by enzymatic ligation (e.g., with $T_4$ DNA ligase), thus converting the probes to circularly-closed molecules which are catenated to the specific target sequences (see e.g., Nilsson, et al., 1994. *Science* 265: 2085–2088). The resulting probes are suitable for the simultaneous analysis of many gene sequences both due to their specificity and selectivity for gene sequence variants (see e.g., Lizardi, et al., 1998. *Nat. Genet.* 19: 225–232; Nilsson, et al., 1997. *Nat. Genet.* 16: 252–255) and due to the fact that the resulting reaction products remain localized to the specific target sequences. Moreover, intramolecular ligation of many different probes is expected to be less susceptible to non-specific cross-reactivity than multiplex PCR-based methodologies where non-cognate pairs of primers can give rise to irrelevant amplification products (see e.g., Landegren and Nilsson, 1997. *Ann. Med.* 29: 585–590).

The starting library can be either single-stranded or double-stranded, as long as it includes a region that, if present in the library, is available for annealing, or can be made available for annealing, to an anchor primer sequence. When used as a template for rolling circle amplification, a region of the double-stranded template needs to be at least transiently single-stranded in order to act as a template for extension of the anchor primer.

Library templates can include multiple elements, including, but not limited to, one or more regions that are complementary to the anchor primer. For example, the template libraries may include a region complementary to a sequencing primer, a control nucleotide region, and an insert sequence comprised of the sequencing template to be subsequently characterized. As is explained in more detail below, the control nucleotide region is used to calibrate the relationship between the amount of byproduct and the number of nucleotides incorporated. As utilized herein the term "complement" refers to nucleotide sequences that are able to hybridize to a specific nucleotide sequence to form a matched duplex.

In one embodiment, a library template includes: (i) two distinct regions that are complementary to the anchor primer, (ii) one region homologous to the sequencing primer, (iii) one optional control nucleotide region, (iv) an insert sequence of, e.g., 30–500, 50–200, or 60–100 nucleotides, that is to be sequenced. The template can, of course, include two, three, or all four of these features.

The template nucleic acid can be constructed from any source of nucleic acid, e.g., any cell, tissue, or organism, and can be generated by any art-recognized method. Suitable methods include, e.g., sonication of genomic DNA and digestion with one or more restriction endonucleases (RE) to generate fragments of a desired range of lengths from an initial population of nucleic acid molecules. Preferably, one or more of the restriction enzymes have distinct four-base recognition sequences. Examples of such enzymes include, e.g., Sau3AI, MspI, and TaqI. Preferably, the enzymes are used in conjunction with anchor primers having regions containing recognition sequences for the corresponding restriction enzymes. In some embodiments, one or both of the adapter regions of the anchor primers contain additional sequences adjoining known restriction enzyme recognition sequences, thereby allowing for capture or annealing to the anchor primer of specific restriction fragments of interest to the anchor primer.

In other embodiments, the restriction enzyme is used with a type IIS restriction enzyme.

Alternatively, template libraries can be made by generating a complementary DNA (cDNA) library from RNA, e.g., messenger RNA (mRNA). The cDNA library can, if desired, be further processed with restriction endonucleases to obtain a 3' end characteristic of a specific RNA, internal fragments, or fragments including the 3' end of the isolated RNA. Adapter regions in the anchor primer may be complementary to a sequence of interest that is thought to occur in the template library, e.g., a known or suspected sequence polymorphism within a fragment generated by endonuclease digestion.

In one embodiment, an indexing oligonucleotide can be attached to members of a template library to allow for subsequent correlation of a template nucleic acid with a population of nucleic acids from which the template nucleic acid is derived. For example, one or more samples of a starting DNA population can be fragmented separately using any of the previously disclosed methods (e.g., restriction digestion, sonication). An indexing oligonucleotide sequence specific for each sample is attached to, e.g., ligated to, the termini of members of the fragmented population. The indexing oligonucleotide can act as a region for circularization, amplification and, optionally, sequencing, which permits it to be used to index, or code, a nucleic acid so as to identify the starting sample from which it is derived.

Distinct template libraries made with a plurality of distinguishable indexing primers can be mixed together for subsequent reactions. Determining the sequence of the member of the library allows for the identification of a sequence corresponding to the indexing oligonucleotide. Based on this information, the origin of any given fragment can be inferred.

Annealing and Amplification of Primer-Template Nucleic Acid Complexes

Libraries of nucleic acids are annealed to anchor primer sequences using recognized techniques (see, e.g., Hatch, et al., 1999. *Genet. Anal. Biomol. Engineer.* 15: 3540; Kool, U.S. Pat. No. 5,714,320 and Lizardi, U.S. Pat. No. 5,854, 033). In general, any procedure for annealing the anchor primers to the template nucleic acid sequences is suitable as long as it results in formation of specific, i.e., perfect or nearly perfect, complementarity between the adapter region or regions in the anchor primer sequence and a sequence present in the template library.

A number of in vitro nucleic acid amplification techniques may be utilized to extend the anchor primer sequence. The size of the amplified DNA preferably is smaller than the size of the anchor pad and also smaller than the distance between anchor pads.

The amplification is typically performed in the presence of a polymerase, e.g., a DNA or RNA-directed DNA polymerase, and one, two, three, or four types of nucleotide triphosphates, and, optionally, auxiliary binding proteins. In general, any polymerase capable of extending a primed 3'-OH group can be used a long as it lacks a 3' to 5' exonuclease activity. Suitable polymerases include, e.g., the DNA polymerases from *Bacillus stearothermophilus, Thermus acquaticus, Pyrococcus furiosis, Thermococcus litoralis*, and *Thermus thermophilus*, bacteriophage $T_4$ and $T_7$, and the *E. coli* DNA polymerase I Klenow fragment. Suitable RNA-directed DNA polymerases include, e.g., the reverse transcriptase from the Avian Myeloblastosis Virus, the reverse transcriptase from the Moloney Murine Leukemia Virus, and the reverse transcriptase from the Human Immunodeficiency Virus-I.

A number of in vitro nucleic acid amplification techniques have been described. These amplification methodologies may be differentiated into those methods: (i) which require temperature cycling—polymerase chain reaction (PCR) (see e.g., Saiki, et al., 1995. *Science* 230: 1350–1354), ligase chain reaction (see e.g., Barany, 1991. *Proc. Natl. Acad. Sci. USA* 88: 189–193; Barringer, et al., 1990. *Gene* 89: 117–122) and transcription-based amplification (see e.g., Kwoh, et al., 1989. *Proc. Natl. Acad Sci USA* 86: 1173–1177) and (ii) isothermal amplification systems—self-sustaining, sequence replication (see e.g., Guatelli, et al., 1990. *Proc. Natl. Acad. Sci. USA* 87: 1874–1878); the Qβ replicase system (see e.g., Lizardi, et al., 1988. *BioTechnology* 6: 1197–1202); strand displacement amplification Nucleic Acids Res. 1992 Apr. 11; 20(7):1691–6; and the methods described in PNAS 1992 Jan. 1; 89(1):392–6; and NASBA J Virol Methods. 1991 December; 35(3):273–86.

Isothermal amplification also includes rolling circle-based amplification (RCA). RCA is discussed in, e.g., Kool, U.S. Pat. No. 5,714,320 and Lizardi, U.S. Pat. No. 5,854,033; Hatch, et al., 1999. *Genet. Anal. Biomol. Engineer.* 15: 35–40. The result of the RCA is a single DNA strand extended from the 3' terminus of the anchor primer (and thus is linked to the solid support matrix) and including a concatamer containing multiple copies of the circular template annealed to a primer sequence. Typically, 1,000 to 10,000 or more copies of circular templates, each having a size of, e.g., approximately 30–500, 50–200, or 60–100 nucleotides size range, can be obtained with RCA.

The product of RCA amplification following annealing of a circular nucleic acid molecule to an anchor primer is shown schematically in FIG. 1A. A circular template nucleic acid 102 is annealed to an anchor primer 104, which has been linked to a surface 106 at its 5' end and has a free 3' OH available for extension. The circular template nucleic acid 102 includes two adapter regions 108 and 110 which are complementary to regions of sequence in the anchor primer 104. Also included in the circular template nucleic acid 102 is an insert 112 and a region 114 homologous to a sequencing primer, which is used in the sequencing reactions described below.

Upon annealing, the free 3'-OH on the anchor primer 104 can be extended using sequences within the template nucleic acid 102. The anchor primer 102 can be extended along the template multiple times, with each iteration adding to the sequence extended from the anchor primer a sequence complementary to the circular template nucleic acid. Four iterations, or four rounds of rolling circle replication, are shown in FIG. 1A as the extended anchor primer amplification product 114. Extension of the anchor primer results in an amplification product covalently or otherwise physically attached to the substrate 106.

Figure 1B:
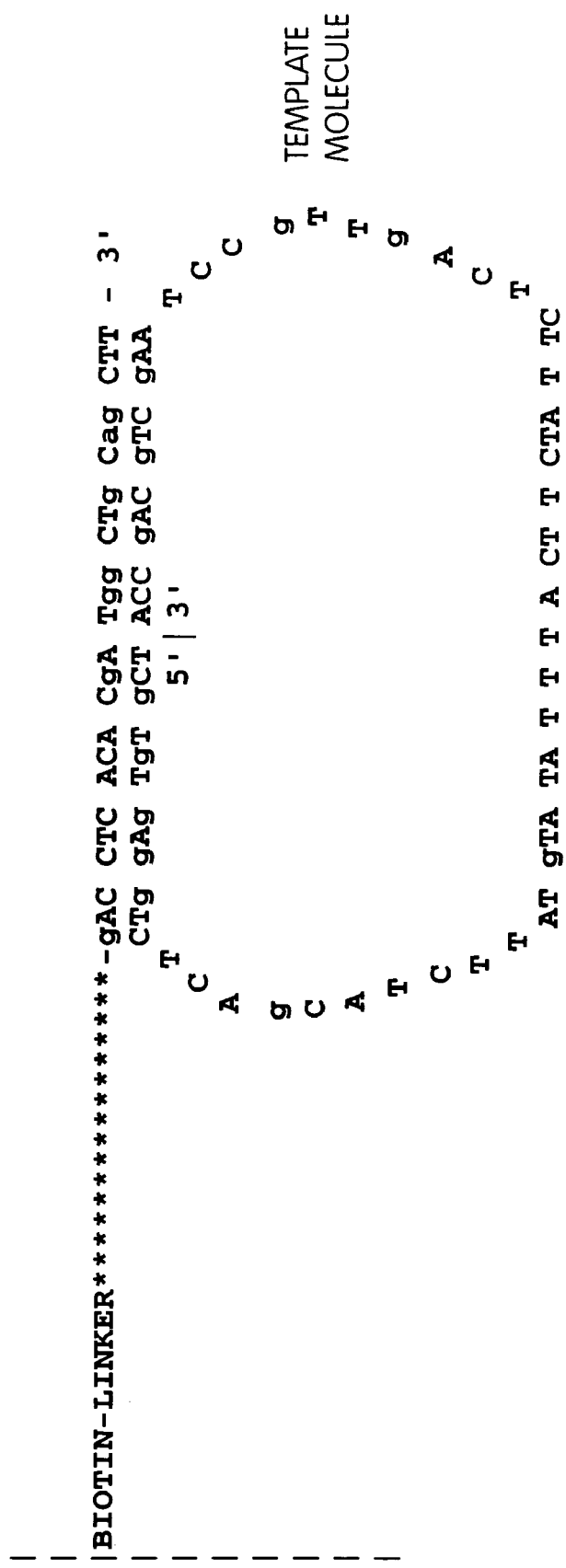

Additional embodiments of circular templates and anchor primers are shown in more detail in FIGS. 1B–1F. FIG. 1B illustrates an annealed open circle linear substrate that can serve, upon ligation, as a template for extension of an anchor primer. A template molecule having the sequence 5'-TCg TgT gAg gTC TCA gCA TCT TAT gTA TAT TTA CTT CTA TTC TCA gTT gCC TAA gCT gCA gCC A-3' (SEQ ID NO:1) is annealed to an anchor primer having a biotin linker at its 5' terminus and the sequence 5'-gAC CTC ACA CgA Tgg CTg CAg CTT-3' (SEQ ID NO:2). Annealing of the template results in juxtaposition of the 5' and 3' ends of the template molecule. The 3'OH of the anchor primer can be extended using the circular template.

Figure 1C:
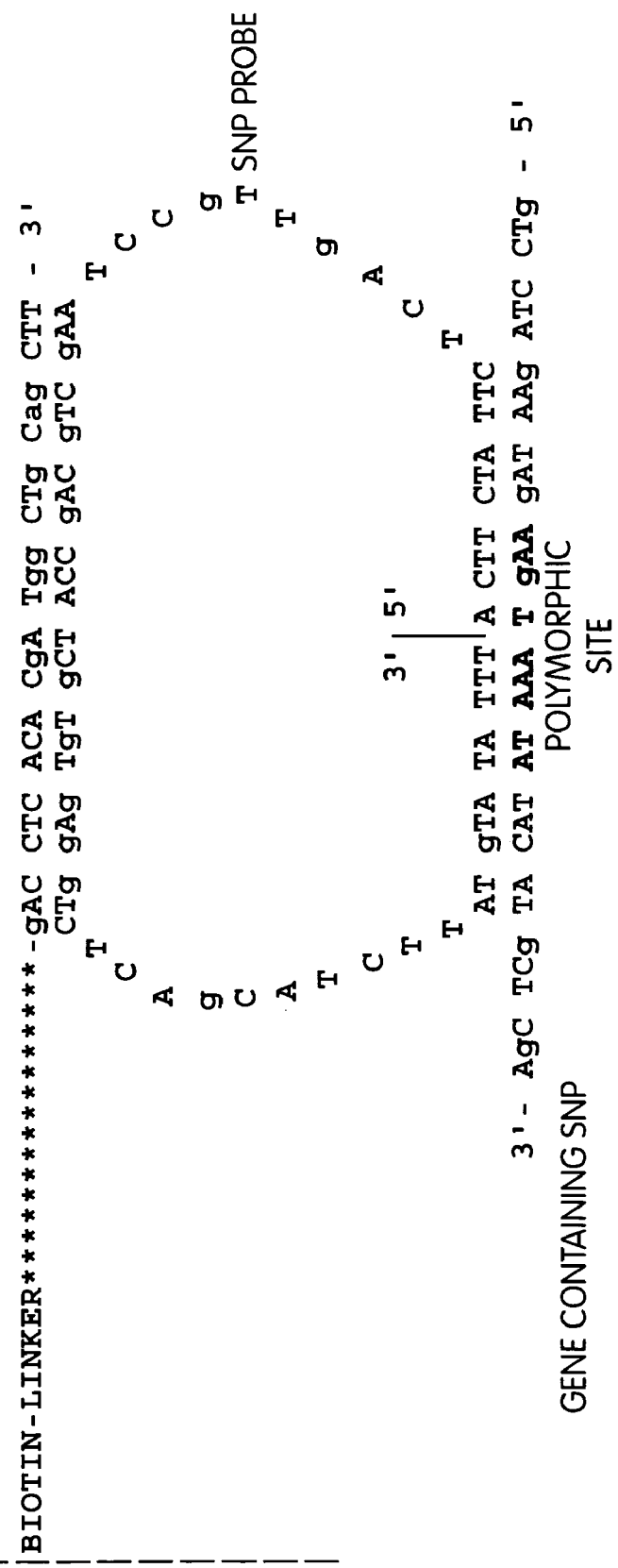

The use of a circular template and an anchor primer for identification of single nucleotide polymorphisms is shown in FIG. 1C. Shown is a generic anchor primer having the sequence 5'-gAC CTC ACA CgA Tgg CTg CAg CTT-3' (SEQ ID NO:3). The anchor primer anneals to an SNP probe having the sequence 5'-TTT ATA TgT ATT CTA CgA CTC Tgg AgT gTg CTA CCg ACg TCg AAt CCg TTg ACT CTT ATC TTC A-3 (SEQ ID NO:4). The SNP probe in turns hybridizes to a region of a SNP-containing region of a gene having the sequence 5'-CTA gCT CgT ACA TAT AAA TgA AgA TAA gAT CCT g-3' (SEQ ID NO:5). Hybridization of a nucleic acid sequence containing the polymorphism to the SNP probe complex allows for subsequent ligation and circularization of the SNP probe. The SNP probe is designed so that its 5' and 3' termini anneal to the genomic region so as to abut in the region of the polymorphic site, as is indicated in FIG. 1C. The circularized SNP probe can be subsequently extended and sequenced using the methods described herein. A nucleic acid lacking the polymorphism does not hybridize so as to result in juxtaposition of the 5' and 3' termini of the SNP probe. In this case, the SNP probe cannot be ligated to form a circular substrate needed for subsequent extension.

Figure 1D:
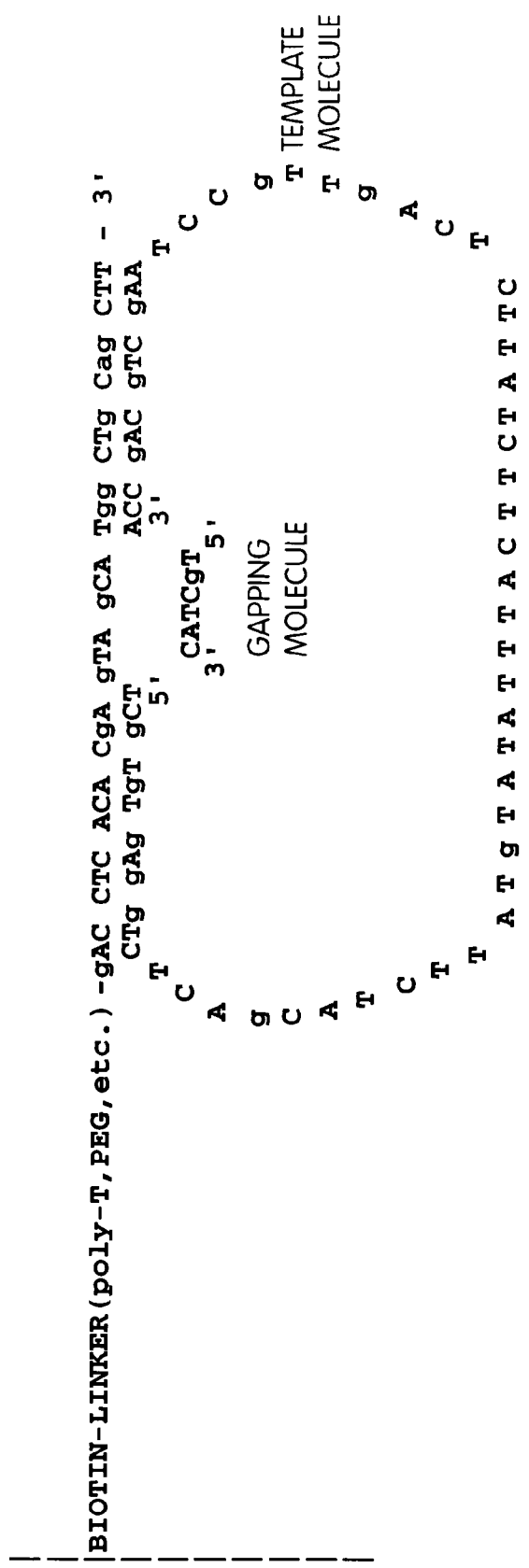

FIG. 1D illustrates the use of a gap oligonucleotide to along with a circular template molecule. An anchor primer having the sequence.)-5'-gAC CTC ACA CgA gTA gCA Tgg CTg CAg CTT-3' (SEQ ID NO:6) is attached to a surface through a biotin linker. A template molecule having the sequence 5'-TCg TgT gAg gTC TCA gCA TCT TAT gTA TAT TTA CTT CTA TTC TCA gTT gCC TAA gCT gCA gCC A-3' (SEQ ID NO:7) is anneals to the anchor primer to result in partially single stranded, or gapped region, in the anchor primer flanked by a double-stranded region. A gapping molecule having the sequence 5'-TgC TAC-3' then anneals to the anchor primer. Ligation of both ends of the gap oligonucleotide to the template molecule results in formation of a circular nucleic acid molecule that can act as a template for rolling circle amplification.

Circular oligonucleotides that are generated during polymerase-mediated DNA replication are dependent upon the relationship between the template and the site of replication initiation. In double-stranded DNA templates, the critical features include whether the template is linear or circular in nature, and whether the site of initiation of replication (i.e., the replication "fork") is engaged in synthesizing both strands of DNA or only one. In conventional double-stranded DNA replication, the replication fork is treated as the site at which the new strands of DNA are synthesized. However, in linear molecules (whether replicated unidirectionally or bidirectionally), the movement of the replication fork(s) generate a specific type of structural motif. If the template is circular, one possible spatial orientation of the replicating molecule takes the form of a θ structure.

Alternatively, RCA can occur when the replication of the duplex molecule begins at the origin. Subsequently, a nick opens one of the strands, and the free 3'-terminal hydroxyl moiety generated by the nick is extended by the action of DNA polymerase. The newly synthesized strand eventually displaces the original parental DNA strand. This aforementioned type of replication is known as rolling-circle replication (RCR) because the point of replication may be envisaged as "rolling around" the circular template strand and, theoretically, it could continue to do so indefinitely. As it progresses, the replication fork extends the outer DNA strand the previous partner. Additionally, because the newly synthesized DNA strand is covalently-bound to the original template, the displaced strand possesses the original genomic sequence (e.g., gene or other sequence of interest) at its 5'-terminus. In rolling-circle replication, the original genomic sequence is followed by any number of "replication units" complementary to the original template sequence, wherein each replication unit is synthesized by continuing revolutions of said original template sequence. Hence, each subsequent revolution displaces the DNA which is synthesized in the previous replication cycle.

In vivo, rolling-circle replication is utilized in several biological systems. For example, the genome of several bacteriophage are single-stranded, circular DNA. During replication, the circular DNA is initially converted to a duplex form, which is then replicated by the aforementioned rolling-circle replication mechanism. The displaced terminus generates a series of genomic units that can be cleaved and inserted into the phage particles. Additionally, the displaced single-strand of a rolling-circle can be converted to duplex DNA by synthesis of a complementary DNA strand. This synthesis can be used to generate the concatemeric duplex molecules required for the maturation of certain phage DNAs. For example, this provides the principle pathway by which λ bacteriophage matures. Rolling-circle replication is also used in vivo to generate amplified rDNA in *Xenopus* oocytes, and this fact may help explain why the amplified rDNA is comprised of a large number of identical repeating units. In this case, a single genomic repeating unit is converted into a rolling-circle. The displaced terminus is then converted into duplex DNA which is subsequently cleaved from the circle so that the two termini can be ligated together so as to generate the amplified circle of rDNA.

Through the use of the RCA reaction, a strand may be generated which represents many tandem copies of the complement to the circularized molecule. For example, RCA has recently been utilized to obtain an isothermal cascade amplification reaction of circularized padlock probes in vitro in order to detect single-copy genes in human genomic DNA samples (see Lizardi, et al., 1998. *Nat. Genet.* 19: 225–232). In addition RCA has also been utilized to detect single DNA molecules in a solid phase-based assay, although difficulties arose when this technique was applied to in situ hybridization (see Lizardi, et al., 1998. *Nat. Genet.* 19: 225–232).

If desired, RCA can be performed at elevated temperatures, e.g., at temperatures greater than 37° C., 42° C., 45° C., 50° C., 60° C., or 70° C. In addition, RCA can be performed initially at a lower temperature, e.g., room temperature, and then shifted to an elevated temperature. Elevated temperature RCA is preferably performed with thermostable nucleic acid polymerases and with primers that can anneal stably and with specificity at elevated temperatures.

RCA can also be performed with non-naturally occurring nucleotides, e.g., peptide nucleic acids. Further, RCA can be performed in the presence of auxiliary proteins such as single-stranded binding proteins.

The development of a method of amplifying short DNA molecules which have been immobilized to a solid support, termed rolling circle amplification (RCA) has been recently described in the literature (see e.g., Hatch, et al., 1999. Rolling circle amplification of DNA immobilized on solid surfaces and its application to multiplex mutation detection. *Genet. Anal. Biomol. Engineer.* 15: 35–40; Zhang, et al., 1998. Amplification of target-specific, ligation-dependent circular probe. Gene 211: 277–85; Baner, et al., 1998. Signal amplification of padlock probes by rolling circle replication. *Nucl. Acids Res.* 26: 5073–5078; Liu, et al., 1995. Rolling circle DNA synthesis: small circular oligonucleotides as efficient templates for DNA polymerase. *J. Am. Chem. Soc.* 118: 1587–1594; Fire and Xu, 1995. Rolling replication of short DNA circles. *Proc. Natl. Acad. Sci. USA* 92: 4641–4645; Nilsson, et al., 1994. Padlock probes: circularizing oligonucleotides for localized DNA detection. *Science* 265: 2085–2088). RCA targets specific DNA sequences through hybridization and a DNA ligase reaction. The circular product is then subsequently used as a template in a rolling circle replication reaction.

Rolling-circle amplification (RCA) driven by DNA polymerase can replicate circularized oligonucleotide probes with either linear or geometric kinetics under isothermal conditions. In the presence of two primers (one hybridizing to the + strand, and the other, to the − strand of DNA), a complex pattern of DNA strand displacement ensues which possesses the ability to generate $1 \times 10^9$ or more copies of each circle in a short period of time (i.e., less-than 90 minutes), enabling the detection of single-point mutations within the human genome. Using a single primer, RCA generates hundreds of randomly-linked copies of a covalently closed circle in several minutes. If solid support matrix-associated, the DNA product remains bound at the site of synthesis, where it may be labeled, condensed, and imaged as a point light source. For example, linear oligonucleotide probes, which can generate RCA signals, have been bound covalently onto a glass surface. The color of the signal generated by these probes indicates the allele status of the target, depending upon the outcome of specific, target-directed ligation events. As RCA permits millions of individual probe molecules to be counted and sorted, it is particularly amenable for the analysis of rare somatic mutations. RCA also shows promise for the detection of padlock probes bound to single-copy genes in cytological preparations.

In addition, a solid-phase RCA methodology has also been developed to provide an effective method of detecting constituents within a solution. Initially, a recognition step is used to generate a complex consisting of a DNA primer duplexed with a circular template is bound to a surface. A polymerase enzyme is then used to amplify the bound complex. RCA uses small DNA probes that are amplified to provide an intense signal using detection methods, including the methods described in more detail below.

Other examples of isothermal amplification systems include, e.g., (i) self-sustaining, sequence replication (see e.g., Guatelli, et al., 1990. *Proc. Natl. Acad. Sci. USA* 87:

1874–1878), (ii) the Qβ replicase system (see e.g., Lizardi, et al., 1988. *BioTechnology* 6: 1197–1202), and (iii) nucleic acid sequence-based amplification (NASBA™; see Kievits, et al., 1991. *J. Virol. Methods* 35: 273–286).

Determining the Nucleotide Sequence of the Sequence Product

Amplification of a nucleic acid template as described above results in multiple copies of a template nucleic acid sequence covalently linked to an anchor primer. In one embodiment, a region of the sequence product is determined by annealing a sequencing primer to a region of the template nucleic acid, and then contacting the sequencing primer with a DNA polymerase and a known nucleotide triphosphate, i.e., dATP, dCTP, dGTP, dTTP, or an analog of one of these nucleotides. The sequence can be determined by detecting a sequence reaction byproduct, as is described below.

The sequence primer can be any length or base composition, as long as it is capable of specifically annealing to a region of the amplified nucleic acid template. No particular structure is required for the sequencing primer is required so long as it is able to specifically prime a region on the amplified template nucleic acid. Preferably, the sequencing primer is complementary to a region of the template that is between the sequence to be characterized and the sequence hybridizable to the anchor primer. The sequencing primer is extended with the DNA polymerase to form a sequence product. The extension is performed in the presence of one or more types of nucleotide triphosphates, and if desired, auxiliary binding proteins.

Incorporation of the dNTP is preferably determined by assaying for the presence of a sequencing byproduct. In a preferred embodiment, the nucleotide sequence of the sequencing product is determined by measuring inorganic pyrophosphate (PPi) liberated from a nucleotide triphosphate (dNTP) as the NTP is incorporated into an extended sequence primer. This method of sequencing, termed Pyrosequencing™ technology PyroSequencing AB, Stockholm, Sweden) can be performed in solution (liquid phase) or as a solid phase technique. PPi-based sequencing methods are described generally in, e.g., WO9813523A1, Ronaghi, et al., 1996. *Anal. Biochem.* 242: 84–89, and Ronaghi, et al., 1998. *Science* 281: 363–365 (1998). These disclosures of PPi sequencing are incorporated herein in their entirety, by reference.

Pyrophosphate released under these conditions can be detected enzymatically (e.g., by the generation of light in the luciferase-luciferin reaction). Such methods enable a nucleotide to be identified in a given target position, and the DNA to be sequenced simply and rapidly while avoiding the need for electrophoresis and the use of potentially dangerous radiolabels.

PPi can be detected by a number of different methodologies, and various enzymatic methods have been previously described (see e.g., Reeves, et al., 1969. *Anal. Biochem.* 28: 282–287; Guillory, et al., 1971. *Anal. Biochem.* 39: 170–180; Johnson, et al., 1968. *Anal. Biochem.* 15: 273; Cook, et al., 1978. *Anal. Biochem.* 91: 557–565; and Drake, et al., 1979. *Anal. Biochem.* 94: 117–120).

PPi liberated as a result of incorporation of a dNTP by a polymerase can be converted to ATP using, e.g., an ATP sulfurylase. This enzyme has been identified as being involved in sulfur metabolism. Sulfur, in both reduced and oxidized forms, is an essential mineral nutrient for plant and animal growth (see e.g., Schmidt and Jager, 1992. *Ann. Rev. Plant Physiol. Plant Mol. Biol.* 43: 325–349). In both plants and microorganisms, active uptake of sulfate is followed by reduction to sulfide. As sulfate has a very low oxidation/reduction potential relative to available cellular reductants, the primary step in assimilation requires its activation via an ATP-dependent reaction (see e.g., Leyh, 1993. *Crit. Rev. Biochem. Mol. Biol.* 28: 515–542). ATP sulfurylase (ATP: sulfate adenylyltransferase; EG 2.7.7.4) catalyzes the initial reaction in the metabolism of inorganic sulfate ($SO_4^{-2}$); see e.g., Robbins and Lipmann, 1958. *J. Biol. Chem.* 233: 686–690; Hawes and Nicholas, 1973. *Biochem. J.* 133: 541–550) In this reaction $SO_4^{-2}$ is activated to adenosine 5'-phosphosulfate (APS).

ATP sulfurylase has been highly purified from several sources, such as *Saccharomyces cerevisiae* (see e.g., Hawes and Nicholas, 1973. *Biochem. J.* 133: 541–550); *Penicillium chrysogenum* (see e.g., Renosto, et al., 1990. *J. Biol. Chem.* 265: 10300–10308); rat liver (see e.g., Yu, et al., 1989. *Arch. Biochem. Biophys.* 269: 165–174); and plants (see e.g., Shaw and Anderson, 1972. *Biochem. J.* 127: 237–247; Osslund, et al., 1982. *Plant Physiol.* 70: 3945). Furthermore, ATP sulfurylase genes have been cloned from prokaryotes (see e.g., Leyh, et al., 1992. *J. Biol. Chem.* 267: 10405–10410; Schwedock and Long, 1989. *Mol. Plant. Microbe Interaction* 2: 181–194; Laue and Nelson, 1994. *J. Bacteriol.* 176: 3723–3729); eukaryotes (see e.g., Cherest, et al., 1987. *Mol. Gen. Genet.* 210: 307–313; Mountain and Korch, 1991. *Yeast* 7: 873–880; Foster, et al., 1994. *J. Biol. Chem.* 269: 19777–19786); plants (see e.g., Leustek, et al., 1994. *Plant Physiol.* 105: 897–90216); and animals (see e.g., Li, et al., 1995. *J. Biol. Chem.* 270: 29453–29459). The enzyme is a homo-oligomer or heterodimer, depending upon the specific source (see e.g., Leyh and Suo, 1992. *J. Biol. Chem.* 267: 542–545).

In some embodiments, a thermostable sulfurylase is used. Thermostable sulfurylases can be obtained from, e.g., *Archaeoglobus* or *Pyrococcus* spp. Sequences of thermostable sulfurylases are available at database Acc. No. 028606, Acc. No. Q9YCR4, and Acc. No. P56863.

ATP sulfurylase has been used for many different applications, for example, bioluminometric detection of ADP at high concentrations of ATP (see e.g., Schultz, et al., 1993. *Anal. Biochem.* 215: 302–304); continuous monitoring of DNA polymerase activity (see e.g., Nyrbn, 1987. *Anal. Biochem.* 167: 235–238); and DNA sequencing (see e.g., Ronaghi, et al., 1996. *Anal. Biochem.* 242: 84–89; Ronaghi, et al., 1998. *Science* 281: 363–365; Ronaghi, et al., 1998. *Anal. Biochem.* 267: 65–71).

Several assays have been developed for detection of the forward ATP sulfurylase reaction. The colorimetric molybdolysis assay is based on phosphate detection (see e.g., Wilson and Bandurski, 1958. *J. Biol. Chem.* 233: 975–981), whereas the continuous spectrophotometric molybdolysis assay is based upon the detection of NADH oxidation (see e.g., Seubert, et al., 1983. *Arch. Biochem. Biophys.* 225: 679–691; Seubert, et al., 1985. *Arch. Biochem. Biophys.* 240: 509–523). The later assay requires the presence of several detection enzymes. In addition, several radioactive assays have also been described in the literature (see e.g., Daley, et al., 1986. *Anal. Biochem.* 157: 385–395). For example, one assay is based upon the detection of $^{32}$PPi released from $^{32}$P-labeled ATP (see e.g., Seubert, et al., 1985. *Arch. Biochem. Biophys.* 240: 509–523) and another on the incorporation of $^{35}$S into [$^{35}$S]-labeled APS (this assay also requires purified APS kinase as a coupling enzyme; see e.g., Seubert, et al., 1983. *Arch. Biochem. Biophys.* 225: 679–691); and a third reaction depends upon the release of $^{35}SO_4^{-2}$ from [$^{35}$S]-labeled APS (see e.g., Daley, et al., 1986. *Anal. Biochem.* 157: 385–395).

For detection of the reversed ATP sulfurylase reaction a continuous spectrophotometric assay (see e.g., Segel, et al., 1987. *Methods Enzymol.* 143: 334–349); a bioluminometric assay (see e.g., Balharry and Nicholas, 1971. *Anal. Biochem.* 40: 1–17); an $^{35}SO_4^{-2}$ release assay (see e.g., Seubert, et al., 1985. *Arch. Biochem. Biophys.* 240: 509–523); and a $^{32}$PPi incorporation assay (see e.g., Osslund, et al., 1982. *Plant Physiol.* 70: 3945) have been previously described.

ATP produced by an ATP sulfurylase can be hydrolyzed using enzymatic reactions to generate light. Light-emitting chemical reactions (i.e., chemiluminescence) and biological reactions (i.e., bioluminescence) are widely used in analytical biochemistry for sensitive measurements of various metabolites. In bioluminescent reactions, the chemical reaction that leads to the emission of light is enzyme-catalyzed. For example, the luciferin-luciferase system allows for specific assay of ATP and the bacterial luciferase-oxidoreductase system can be used for monitoring of NAD(P)H. Both systems have been extended to the analysis of numerous substances by means of coupled reactions involving the production or utilization of ATP or NAD(P)H (see e.g., Kricka, 1991. Chemiluminescent and bioluminescent techniques. *Clin. Chem.* 37: 1472–1281).

The development of new reagents have made it possible to obtain stable light emission proportional to the concentrations of ATP (see e.g., Lundin, 1982. Applications of firefly luciferase In; *Luminescent Assays* (Raven Press, New York) or NAD(P)H (see e.g., Lovgren, et al., Continuous monitoring of NADH-converting reactions by bacterial luminescence. *J. Appl. Biochem.* 4: 103–111). With such stable light emission reagents, it is possible to make end-point assays and to calibrate each individual assay by addition of a known amount of ATP or NAD(P)H. In addition, a stable light-emitting system also allows continuous monitoring of ATP- or NAD(P)H-converting systems.

Suitable enzymes for converting ATP into light include luciferases, e.g., insect luciferases. Luciferases produce light as an end-product of catalysis. The best known light-emitting enzyme is that of the firefly, *Photinus pyralis (Coleoptera)*. The corresponding gene has been cloned and expressed in bacteria (see e.g., de Wet, et al., 1985. *Proc. Natl. Acad. Sci USA* 80: 7870–7873) and plants (see e.g., Ow, et al., 1986. *Science* 234: 856–859), as well as in insect (see e.g., Jha, et al. 1990. *FEBS Lett.* 274: 24–26) and mammalian cells (see e.g., de Wet, et al., 1987. *Mol. Cell. Biol.* 7: 725–7373; Keller, et al., 1987. *Proc. Natl. Acad. Sci. USA* 82: 3264–3268). In addition, a number of luciferase genes from the Jamaican click beetle, *Pyroplorus plagiophihalamus (Coleoptera)*, have recently been cloned and partially characterized (see e.g., Wood, et al., 1989. *J. Biolumin. Chemilumin.* 4: 289–301; Wood, et al., 1989. *Science* 244: 700–702). Distinct luciferases can sometimes produce light of different wavelengths, which may enable simultaneous monitoring of light emissions at different wavelengths. Accordingly, these aforementioned characteristics are unique, and add new dimensions with respect to the utilization of current reporter systems.

Firefly luciferase catalyzes bioluminescence in the presence of luciferin, adenosine 5'-triphosphate (ATP), magnesium ions, and oxygen, resulting in a quantum yield of 0.88 (see e.g., McElroy and Selinger, 1960. *Arch. Biochem. Biophys.* 88: 136–145). The firefly luciferase bioluminescent reaction can be utilized as an assay for the detection of ATP with a detection limit of approximately $1\times10^{-13}$ M (see e.g., Leach, 1981. *J. Appl. Biochem.* 3: 473–517). In addition, the overall degree of sensitivity and convenience of the luciferase-mediated detection systems have created considerable interest in the development of firefly luciferase-based biosensors (see e.g., Green and Kricka, 1984. *Talanta* 31: 173–176; Blum, et al., 1989. *J. Biolumin. Chemilumin.* 4: 543–550).

Using the above-described enzymes, the sequence primer is exposed to a polymerase and a known dNTP. If the dNTP is incorporated onto the 3' end of the primer sequence, the dNTP is cleaved and a PPi molecule is liberated. The PPi is then converted to ATP with ATP sulfurylase. Preferably, the ATP sulfurylase is present at a sufficiently high concentration that the conversion of PPi proceeds with first-order kinetics with respect to PPi. In the presence of luciferase, the ATP is hydrolyzed to generate a photon. The reaction preferably has a sufficient concentration of luciferase present within the reaction mixture such that the reaction, ATP→ADP+$PO_4^{3-}$+photon (light), proceeds with first-order kinetics with respect to ATP. The photon can be measured using methods and apparatuses described below.

For most applications it is desirable to wash away diffusible sequencing reagents, e.g., unincorporated dNTPs, with a wash buffer. Any wash buffer used in pyrophosphate sequencing can be used.

In some embodiments, the concentration of reactants in the sequencing reaction include 1 pmol DNA, 3 pmol polymerase, 40 pmol dNTP in 0.2 ml buffer. See Ronaghi, et al., *Anal. Biochem.* 242: 84–89 (1996).

The sequencing reaction can be performed with each of four predetermined nucleotides, if desired. A "complete" cycle generally includes sequentially administering sequencing reagents for each of the nucleotides dATP, dGTP, dCTP and dTTP (or dUTP), in a predetermined order. Unincorporated dNTPs are washed away between each of the nucleotide additions. Alternatively, unincorporated dNTPs are degraded by apyrase (see below). The cycle is repeated as desired until the desired amount of sequence of the sequence product is obtained. In some embodiments, about 10–1000, 10–100, 10–75, 20–50, or about 30 nucleotides of sequence information is obtained from extension of one annealed sequencing primer.

Luciferase can hydrolyze dATP directly with concomitant release of a photon. This results in a false positive signal because the hydrolysis occurs independent of incorporation of the dATP into the extended sequencing primer. To avoid this problem, a dATP analog can be used which is incorporated into DNA, i.e., it is a substrate for a DNA polymerase, but is not a substrate for luciferase. One such analog is α-thio-dATP. Thus, use of α-thio-dATP avoids the spurious photon generation that can occur when dATP is hydrolyzed without being incorporated into a growing nucleic acid chain.

Typically, the PPi-based detection is calibrated by the measurement of the light released following the addition of control nucleotides to the sequencing reaction mixture immediately after the addition of the sequencing primer. This allows for normalization of the reaction conditions. Incorporation of two or more identical nucleotides in succession is revealed by a corresponding increase in the amount of light released. Thus, a two-fold increase in released light relative to control nucleotides reveals the incorporation of two successive dNTPs into the extended primer.

If desired, apyrase may be "washed" or "flowed" over the surface of the solid support so as to facilitate the degradation of any remaining, non-incorporated dNTPs within the sequencing reaction mixture. Upon treatment with apyrase, any remaining reactants are washed away in preparation for the following dNTP incubation and photon detection steps. Alternatively, the apyrase may be bound to the solid support.

When the support is planar, the pyrophosphate sequencing reactions preferably take place in a thin reaction chamber that includes one optically-transparent solid support surface and an optically-transparent cover. Sequencing reagents may then be delivered by flowing them across the surface of the substrate. When the support is not planar, the reagents may be delivered by dipping the solid support into baths of any given reagents.

When the support is in the form of a cavitated array, e.g., in the termini of a fiber optic reactor array (FORA), suitable delivery methods for reagents include, e.g., flowing spraying, electrospraying, ink jet delivery, stamping, ultrasonic atomization (Sonotek Corp., Milton, N.Y.) and rolling. Preferably, all reagent solutions contain 10–20% ethylene glycol to minimize evaporation. When spraying is used, reagents are delivered to the FORA surface in a homogeneous thin layer produced by industrial type spraying nozzles (Spraying Systems, Co., Wheaton, Ill.) or atomizers used in thin layer chromatography (TLC), such as CAMAG TLC Sprayer (Camag Scientific Inc., Wilmington, N.C.). These sprayers atomize reagents into aerosol spray particles in the size range of 0.3 to 10 µm.

Electrospray deposition (ESD) of protein and DNA solutions is currently used to generate ions for mass spectrometric analysis of these molecules. Deposition of charged electrospray products on certain areas of a FORA substrate under control of electrostatic forces is suggested. It was also demonstrated that the ES-deposited proteins and DNA retain their ability to specifically bind antibodies and matching DNA probes, respectively, enabling use of the ESD fabricated matrixes in Dot Immuno-Binding (DIB) and in DNA hybridization assays. (Morozov V N, Morozova T Y: Electrospray deposition as a method for mass fabrication of mono- and multicomponent microarrays of biological and biologically active substances. Anal Chem 1999 Aug. 1; 71(15):3110–7)

Ink-jet delivery is applicable to protein solutions and other biomacromolecules, as documented in the literature (e.g. Roda A, Guardigli M, Russo C, Pasini P, Baraldini M., Protein microdeposition using a conventional ink-jet printer. Biotechniques 2000 March; 28(3): 492–6). It is also commercially available e.g. from MicroFab Technologies, Inc. (Plano, Tex.).

Reagent solutions can alternatively be delivered to the FORA surface by a method similar to lithography. Rollers (stamps; hydrophilic materials should be used) would be first covered with a reagent layer in reservoirs with dampening sponges and then rolled over (pressed against) the FORA surface.

Successive reagent delivery steps are preferably separated by wash steps. These washes can be performed, e.g., using the above described methods, including high-flow sprayers or by a liquid flow over the FORA surface.

In various embodiments, some components of the reaction are immobilized, while other components are provided in solution. For example, in some embodiments, the enzymes utilized in the pyrophosphate sequencing reaction (e.g., sulfurylase, luciferase) may be immobilized if desired onto the solid support. Similarly, one or more of the enzymes utilized in the pyrophosphate sequencing reaction, e.g., sulfurylase, luciferase may be immobilized at the termini of a fiber optic reactor array. Other components of the reaction, e.g., a polymerase (such as Klenow fragment), nucleic acid template, and nucleotides can be added by flowing, spraying, or rolling. In still further embodiments, one more of the reagents used in the sequencing reactions is delivered on beads.

In some embodiments, reagents are dispensed using an expandable, flexible membrane to dispense reagents and seal reactors on FORA surface during extension reactions. Reagents can be sprayed or rolled onto either the FORA surface or onto the flexible membrane. The flexible membrane could then be either rapidly expanded or physically moved into close proximity with the FORA thereby sealing the wells such that PPi would be unable to diffuse from well to well. Preferably, data acquisition takes place at a reasonable time after reaction initiation to allow maximal signal to generate.

A sequence in an extended anchor primer can also be identified using sequencing methods other than by detecting a sequence byproduct. For example, sequencing can be performed by measuring incorporation of labeled nucleotides or other nucleotide analogs. These methods can be used in conjunction with fluorescent or electrochemiluminescent-based methods.

Alternatively, sequence byproducts can be generated using dideoxynucleotides having a label on the 3' carbon. Preferably, the label can be cleaved to reveal a 3' hydroxyl group. In this method, addition of a given nucleotide is scored as positive or negative, and one base is determined at each trial. In this embodiment, solid phase enzymes are not required and multiple measurements can be made.

In another embodiment, the identity of the extended anchor primer product is determined using labeled deoxynucleotides. The labeled deoxynucleotides can be, e.g., fluorescent nucleotides. Preferably the fluorescent nucleotides can be detected following laser-irradiation.

Preferably, the fluorescent label is not stable for long periods of exposure. If desired, the fluorescent signal can be quenched, e.g., photobleached, to return signal to background levels prior to addition of the next base. A preferred electrochemiluminescent label is ruthenium-tris-bi-pyridyl.

When luciferase is immobilized, it is preferably less than 50 µm from an anchored primer.

The photons generated by luciferase may be quantified using a variety of detection apparatuses, e.g., a photomultiplier tube, charge-coupled display (CCD), CMOS, absorbance photometer, a luminometer, charge injection device (CID), or other solid state detector, as well as the apparatuses described herein. In a preferred embodiment, the quantitation of the emitted photons is accomplished by the use of a CCD camera fitted with a fused fiber optic bundle. In another preferred embodiment, the quantitation of the emitted photons is accomplished by the use of a CCD camera fitted with a microchannel plate intensifier. CCD detectors are described in, e.g., Bronks, et al., 1995. *Anal. Chem.* 65: 2750–2757.

An exemplary CCD system is a Spectral Instruments, Inc. (Tucson, Ariz.) Series 600 4-port camera with a Lockheed-Martin LM485 CCD chip and a 1—1 fiber optic connector (bundle) with 6–8 um individual fiber diameters. This system has 4096×4096, or greater than 16 million, pixels and has a quantum efficiency ranging from 10% to >40%. Thus, depending on wavelength, as much as 40% of the photons imaged onto the CCD sensor are converted to detectable electrons.

Apparatuses for Sequencing Nucleic Acids

Also provided in the invention are apparatuses for sequencing nucleic acids. In some embodiments, the apparatuses include anchor primers attached to planar substrates. Nucleic acid sequence information can be detected using conventional optics or fiber-optic based systems attached to the planar substrate. In other embodiments, the apparatuses include anchor primers attached to the termini of fiber-optic arrays. In these embodiments, sequence information can be obtained directly from the termini of the fiber optic array.

Apparatus for Sequencing Nucleic Acids

An apparatus for sequencing nucleic acids is illustrated in FIG. 2. The apparatus includes an inlet conduit 200 in communication with a detachable perfusion chamber 220. The inlet conduit 200 allows for entry of sequencing reagents via a plurality of tubes 202–212, which are each in communication with a plurality of sequencing dispensing reagent vessels 214–224.

Reagents are introduced through the conduit 200 into the perfusion chamber 220 using either a pressurized system or pumps to drive positive flow. Typically, the reagent flow rates are from 0.05 to 50 ml/minute (e.g., 1 to 50 ml/minute) with volumes from 0.100 ml to continuous flow (for washing). Valves are under computer control to allow cycling of nucleotides and wash reagents. Sequencing reagents, e.g., polymerase can be either pre-mixed with nucleotides or added in stream. A manifold brings all six tubes 202–212 together into one for feeding the perfusion chamber. Thus several reagent delivery ports allow access to the perfusion chamber. For example, one of the ports may be utilized to allow the input of the aqueous sequencing reagents, while another port allows these reagents (and any reaction products) to be withdrawn from the perfusion chamber.

The perfusion chamber 200 contains a substrate to which a plurality of anchor primers have been attached. This can be a planar substrate containing one or more anchored primers in anchor pads formed at the termini of a bundled fiber optic arrays. The latter substrate surface is discussed in more detail below.

The perfusion chamber allows for a uniform, linear flow of the required sequencing reagents, in aqueous solution, over the amplified nucleic acids and allows for the rapid and complete exchange of these reagents. Thus, it is suitable for performing pyrophosphate-based sequencing reaction. The perfusion chamber can also be used to prepare the anchor primers and perform amplification reactions, e.g., the RCA reactions described herein.

The solid support is optically linked to an imaging system 230, which includes a CCD system in association with conventional optics or a fiber optic bundle. In one embodiment the perfusion chamber substrate includes a fiber optic array wafer such that light generated near the aqueous interface is transmitted directly to the exterior of the substrate or chamber. When the CCD system includes a fiber optic connector, imaging can be accomplished by placing the perfusion chamber substrate in direct contact with the connector. Alternatively, conventional optics can be used to image the light, e.g., by using a 1—1 magnification high numerical aperture lens system, from the exterior of the fiber optic substrate directly onto the CCD sensor. When the substrate does not provide for fiber optic coupling, a lens system can also be used as described above, in which case either the substrate or the perfusion chamber cover is optically transparent. An exemplary CCD imaging system is described above.

The imaging system 230 is used to collect light from the reactors on the substrate surface. Light can be imaged, for example, onto a CCD using a high sensitivity low noise apparatus known in the art. For fiber-optic based imaging, it is preferable to incorporate the optical fibers directly into the cover slip.

The imaging system is linked to a computer control and data collection system 240. In general, any commonly available hardware and software package can be used. The computer control and data collection system is also linked to the conduit 200 to control reagent delivery.

Figure 3:
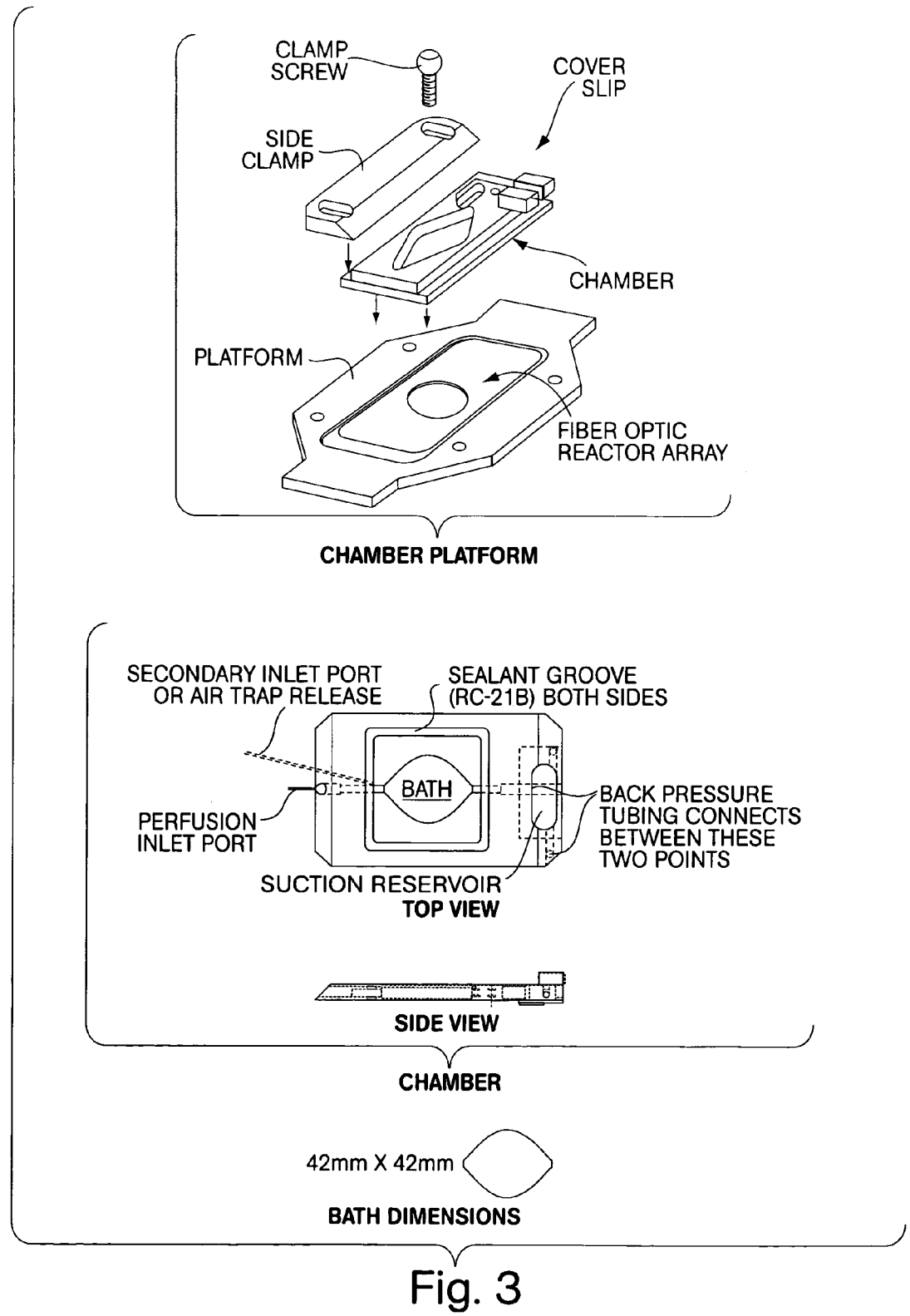
FIG. 3 is a drawing of a perfusion chamber according to the present invention.

An example of a perfusion chamber of the present invention is illustrated in FIG. 3. The perfusion chamber includes a sealed compartment with transparent upper and lower slide. It is designed to allow linear flow of solution over the surface of the substrate surface and to allow for fast exchange of reagents. Thus, it is suitable for carrying out, for example, the pyrophosphate sequencing reactions. Laminar flow across the perfusion chamber can be optimized by decreasing the width and increasing the length of the chamber.

The perfusion chamber is preferably detached form the imaging system while it is being prepared and only placed on the imaging system when sequencing analyses is performed.

In one embodiment, the solid support (i.e., a DNA chip or glass slide) is held in place by a metal or plastic housing, which may be assembled and disassembled to allow replacement of said solid support.

The lower side of the solid support of the perfusion chamber carries the reaction center array and, with a traditional optical-based focal system, a high numerical aperture objective lens is used to focus the image of the reaction center array onto the CCD imaging system.

The photons generated by the pyrophosphate sequencing reaction are captured by the CCD only if they pass through a focusing device (e.g., an optical lens or optical fiber) and are focused upon a CCD element. However, the emitted photons should escape equally in all directions. In order to maximize their subsequent "capture" and quantitation when utilizing a planar array (e.g., a DNA chip), it is preferable to collect the photons immediately at the planar solid support. This is accomplished by either: (i) utilizing optical immersion oil between the cover slip and a traditional optical lens or optical fiber bundle or, preferably, (ii) incorporating optical fibers directly into the cover slip itself. Similarly, when a thin, optically-transparent planar surface is used, the optical fiber bundle can also be placed against its back surface, eliminating the need to "image" through the depth of the entire reaction/perfusion chamber.

In one aspect, the invention embodies an apparatus for processing a plurality of analytes, the apparatus comprising: a flow chamber having therein a substrate comprising a plurality of cavitated surfaces that have thereon nucleic acid molecules; fluid means for delivering processing reagents from one or more reservoirs to the flow chamber so that the analytes anchored to the plurality of microparticles are exposed to the reagents; and detection means for detecting a sequence of optical signals from each microparticle of the plurality, each optical signal of the sequence being indicative of an interaction between a processing reagent and the analyte anchored thereto, wherein the detection means is in communication with the cavitated surfaces. The detection means may further comprise signal tracking means for correlating said optical signals from each of the microparticles in each of the digital images to form a sequence. The signal tracking means may comprise a CCD camera, and the analyte may comprise DNA.

Fiber Optic Substrate Arrays with Linked Anchor Primers

In some embodiments, the solid support is coupled to a bundle of optical fibers that are used to detect and transmit sequence reaction of byproducts. The total number of optical fibers within the bundle may be varied so as to match the number of individual arrays utilized in the sequencing reaction. The number of optical fibers incorporated into the bundle is designed to match the CCD (i.e., approximately 60 mm×60 mm) so as to allow 1:1 imaging. The desired number of optical fibers are initially fused into a bundle, the terminus of which is cut and polished so as to form a "wafer" of the required thickness (e.g., 1.5 mm). The resulting optical fiber wafers possess similar handling properties to that of a plane of glass. The individual fibers can be any size diameter (e.g., 3 µm to 100 µm).

In some embodiments two fiber optic bundles are used: a first bundle is attached directly to the CCD sensor (the fiber bundle or connector or solid support) and a second bundle is used as the perfusion chamber substrate (the wafer or substrate). In this case the two are placed in direct contact, optionally with the use of optical coupling fluid, in order to image the reaction centers onto the CCD sensor. The overall sizes of the bundles are chosen so as to optimize the usable area of the CCD while maintaining desirable reagent (flow) characteristics in the perfusion chamber. Thus for a 4096× 4096 pixel CCD array with 15 um pixels, the fiber bundle is chosen to be approximately 60 mm×60 mm or to have a diameter of approximately 90 mm. The wafer could be slightly larger in order to maximize the use of the CCD area, or slightly smaller in order to match the format of a typical microscope slide—25 mm×75 mm. The diameters of the individual fibers within the bundles are chosen so as to maximize the probability that a single reaction will be imaged onto a single CCD pixel, within the constraints of the state of the art. Exemplary diameters are 6–8 um for the fiber bundle and 6–50 um for the wafer, though any diameter in the range 3–100 um can be used. The fiber bundle is obtained commercially from the CCD camera manufacturer. The wafer can be obtained from Incom, Inc. (Charlton, Mass.) and is cut and polished from a large fusion of fiber optics, typically being 2 mm thick, though possibly being 0.5 to 5 mm thick. The wafer has handling properties similar to a pane of glass or a glass microscope slide.

Figure 4:
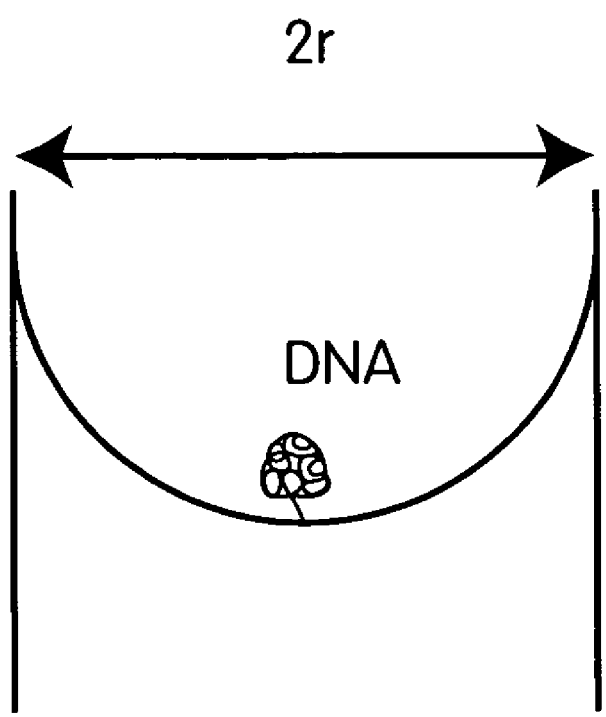
FIG. 4 is a drawing of a cavitated fiber optic terminus of the present invention.

In other embodiments, the planar support is omitted and the anchor primers are linked directly to the termini of the optical fibers. Preferably, the anchor primers are attached to termini that are cavitated as shown schematically in FIG. 4. The termini are treated, e.g., with acid, to form an indentation in the fiber optic material, wherein the indentation ranges in depth from approximately one-half the diameter of an individual optical fiber up to two to three times the diameter of the fiber.

Cavities can be introduced into the termini of the fibers by placing one side of the optical fiber wafer into an acid bath for a variable amount of time. The amount of time can vary depending upon the overall depth of the reaction cavity desired (see e.g., Walt, et al., 1996. *Anal. Chem.* 70: 1888). Several methods are known in the art for attaching molecules (and detecting the attached molecules) in the cavities etched in the ends of fiber optic bundles. See, e.g., Michael, et al., *Anal. Chem.* 70: 1242–1248 (1998); Ferguson, et al., *Nature Biotechnology* 14: 1681–1684 (1996); Healey and Walt, *Anal. Chem.* 69: 2213–2216 (1997). A pattern of reactive sites can also be created in the microwell, using photolithographic techniques similar to those used in the generation of a pattern of reaction pads on a planar support. See, Healey, et al., *Science* 269: 1078–1080 (1995); Munkholm and Walt, *Anal. Chem.* 58: 1427–1430 (1986), and Bronk, et al., *Anal. Chem.* 67: 2750–2757 (1995).

The opposing side of the optical fiber wafer (i.e., the non-etched side) is highly polished so as to allow optical-coupling (e.g., by immersion oil or other optical coupling fluids) to a second, optical fiber bundle. This second optical fiber bundle exactly matches the diameter of the optical wafer containing the reaction chambers, and serve to act as a conduit for the transmission of the photons, generated by the pyrophosphate sequencing reaction, to its attached CCD imaging system or camera.

The surface of the fiber optic wafer is preferably coated to facilitate its use in the sequencing reactions. A coated surface is preferably optically transparent, allows for easy chemical modification of attached proteins and nucleic acids, and does not negatively affect the activity of immobilized proteins. In addition, the surface preferably minimizes non-specific absorption of macromolecules and increases the stability of linked macromolecules (e.g., attached nucleic acids and proteins).

Suitable materials for coating the array include, e.g., plastic (e.g. polystyrene). The plastic can be preferably spin-coated or sputtered (0.1 µm thickness). Other materials for coating the array include gold layers, e.g. 24 karat gold, 0.1 µm thickness, with adsorbed self-assembling monolayers of long chain thiol alkanes. Biotin is then coupled covalently to the surface and saturated with a biotin-binding protein (e.g. streptavidin).

Coating materials can additionally include those systems used to attach an anchor primer to a substrate. Organosilane reagents, which allow for direct covalent coupling of proteins via amino, sulfhydryl or carboxyl groups, can also be used to coat the array. Additional coating substances include photoreactive linkers, e.g. photobiotin, (Amos et al., "Biomaterial Surface Modification Using Photochemical Coupling Technology," in *Encyclopedic Handbook of Biomaterials and Bioengineering, Part A: Materials*, Wise et al. (eds.), New York, Marcel Dekker, pp. 895926, 1995).

Additional coating materials include hydrophilic polymer gels (polyacrylamide, polysaccharides), which preferably polymerize directly on the surface or polymer chains covalently attached post polymerization (Hjerten, J., J. Chromatogr. 347,191 (1985); Novotny, M., Anal. Chem. 62,2478 (1990), as well as pluronic polymers (triblock copolymers, e.g. PPO-PEO-PPO, also known as F-108), specifically adsorbed to either polystyrene or silanized glass surfaces (Ho et al., *Langmuir* 14:3889–94, 1998), as well as passively adsorbed layers of biotin-binding proteins.

In addition, any of the above materials can be derivatized with metal chelating groups (e.g. nitrilo triacetic acid, iminodiacetic acid, pentadentate chelator), which will bind 6×His-tagged proteins and nucleic acids.

In a preferred embodiment, the individual optical fibers utilized to generate the fused optical fiber bundle/wafer are larger in diameter (i.e., 6 µm to 12 µm) than those utilized in the optical imaging system (i.e., 3 µm). Thus, several of the optical imaging fibers can be utilized to image a single reaction site.

The etched, hemispherical geometry reduces background signal from the $PP_i$ released from adjacent anchor pads. In contrast to use of a "chip"-based geometry, wherein the required sequencing reagents are "flowed" over the surface of the solid support matrix (i.e., the anchor pads), delivery of the various sequencing reagents in acid-etched optical fiber wafer embodiment is performed by immersion of the acid-etched cavities, alternately, into dNTP/APS/sulfurylase reagents and then, subsequently, into the apyrase reagents to facilitate the degradation of any remaining dNTPs.

Mathematical Analysis Underlying Optimization of the Pyrophosphate Sequencing Reaction While not wishing to be bound by theory, it is believed that optimization of reaction conditions can be performed using assumptions underlying the following analyses.

Solid-phase pyrophosphate sequencing was initially developed by combining a solid-phase technology and a sequencing-by-synthesis technique utilizing bioluminescence (see e.g., Ronaghi, et al., 1996. Real-time DNA sequencing using detection of pyrophosphate release. *Anal. Biochem.* 242: 84–89). In the solid-phase methodology, an immobilized, primed DNA strand is incubated with DNA polymerase, ATP sulfurylase, and luciferase. By stepwise nucleotide addition with intermediate washing, the event of sequential polymerization can be followed. The signal-to-noise ratio was increased by the use of α-thio dATP in the system. This dATP analog is efficiently incorporated by DNA polymerase but does not serve as a substrate for luciferase. This reduces background fluorescence and facilitates performance of the sequencing reaction in real-time. In these early studies, sequencing of a PCR product using streptavidin-coated magnetic beads as a solid support was presented. However, it was found that the loss of the beads during washing, which was performed between each nucleotide and enzyme addition, limited the technique to short sequences.

Currently, pyrophosphate sequencing methodologies have a reasonably well-established history for ascertaining the DNA sequence from many identical copies of a single DNA sequencing template (see e.g., Ronaghi, et al., 1996. Real-Time DNA Sequencing Using Detection of Pyrophosphate Release, *Anal. Biochem.* 242: 84–89; Nyrén, et al., Method of Sequencing DNA, patent WO9813523A1 (issued Apr. 2, 1998; filed Sep. 26, 1997); Ronaghi, et al., 1998. A Sequencing Method Based on Real-Time Pyrophosphate *Science* 281: 363–365 (1998). Pyrophosphate (PPi)-producing reactions can be monitored by a very sensitive technique based on bioluminescence (see e.g., Nyrén, et al., 1996. pp. 466–496 (*Proc. 9$^{th}$ Inter. Symp. Biolumin. Chemilumin.*). These bioluminometric assays rely upon the detection of the PPi released in the different nucleic acid-modifying reactions. In these assays, the PPi which is generated is subsequently converted to ATP by ATP sulfurylase and the ATP production is continuously monitored by luciferase. For example, in polymerase-mediated reactions, the PPi is generated when a nucleotide is incorporated into a growing nucleic acid chain being synthesized by the polymerase. While generally, a DNA polymerase is utilized to generate PPi during a pyrophosphate sequencing reaction (see e.g., Ronaghi, et al., 1998. *Doctoral Dissertation*, The Royal Institute of Technology, Dept. of Biochemistry (Stockholm, Sweden)), it is also possible to use reverse transcriptase (see e.g., Karamohamamed, et al., 1996. pp. 319–329 (*Proc. 9$^{th}$ Inter. Symp. Biolumin. Chemilumin.*) or RNA polymerase (see e.g., Karamohamamed, et al., 1998. *BioTechniques* 24: 302–306) to follow the polymerization event.

For example, a bioluminometric primer extension assay has been utilized to examine single nucleotide mismatches at the 3'-terminus (see e.g., Nyrén, et al., 1997. *Anal. Biochem.* 244: 367–373). A phage promoter is typically attached onto at least one of the arbitrary primers and, following amplification, a transcriptional unit may be obtained which can then be subjected to stepwise extension by RNA polymerase. The transcription-mediated PPi-release can then be detected by a bioluminometric assay (e.g., ATP sulfurylase-luciferase). By using this strategy, it is likely to be possible to sequence double-stranded DNA without any additional specific sequencing primer. In a series of "run-off" assays, the extension by $T_7$ phage RNA polymerase has been examined and was found to be rather slow (see e.g., Kwok, et al., 1990. *Nucl. Acids Res.* 18: 999–1005). The substitution of an α-thio nucleotide analogs for the subsequent, correct natural deoxynucleotide after the 3'-mismatch termini, could decrease the rate of polymerization by 5-fold to 13-fold. However, after incorporation of a few bases, the rate of DNA synthesis is comparable with the rate observed for a normal template/primer.

Single-base detection by this technique has been improved by incorporation of apyrase to the system, which catalyzes NTP hydrolysis and reduces the nucleotide concentration far below the $K_m$ of DNA polymerase. The use of apyrase minimizes further extension upon contact with a mismatched base, and thereby simplifies the data analysis. The above-described technique provides a rapid and real-time analysis for applications in the areas of mutation detection and single-nucleotide polymorphism (SNP) analysis.

The pyrophosphate sequencing system uses reactions catalyzed sequentially by several enzymes to monitor DNA synthesis. Enzyme properties such as stability, specificity, sensitivity, $K_M$ and $K_{CAT}$ are important for the optimal performance of the system. In the pyrophosphate sequencing system, the activity of the detection enzymes (i.e., sulfurylase and luciferase) generally remain constant during the sequencing reaction, and are only very slightly inhibited by high amounts of products (see e.g., Ronaghi, et al., 1998. *Doctoral Dissertation*, The Royal Institute of Technology, Dept. of Biochemistry (Stockholm, Sweden)). Sulfurylase converts PPi to ATP in approximately 2.0 seconds, and the generation of light by luciferase takes place in less than 0.2 seconds. The most critical reactions are the DNA polymerization and the degradation of nucleotides. The value of constants characterizing the enzymes utilized in the pyrophosphate sequencing methodology are listed below:

| Enzyme | $K_M$ (µM) | $K_{CAT}$ (S$^{-1}$) |
|---|---|---|
| Klenow | 0.18 (dTTP) | 0.92 |
| $T_7$ DNA Polymerase | 0.36 (dTTP) | 0.52 |
| ATP Sulfurylase | 0.56 (APS); 7.0 (PPi) | 38 |
| Firefly Luciferase | 20 (ATP) | 0.015 |
| Apyrase | 120 (ATP); 260 (ADP) | 500 (ATP) |

The enzymes involved in these four reactions compete for the same substrates. Therefore, changes in substrate concentrations are coupled. The initial reaction is the binding of a dNTP to a polymerase/DNA complex for chain elongation. For this step to be rapid, the nucleotide triphosphate concentration must be above the $K_M$ of the DNA polymerase. If the concentration of the nucleotide triphosphates is too high, however, lower fidelity of the polymerase may be observed (see e.g., Cline, et al., 1996. PCR fidelity of Pfu DNA polymerase and other thermostable DNA polymerases. *Nucl. Acids Res.* 24: 3546–3551). A suitable range of concentrations is established by the $K_M$ for the misincorporation, which is usually much higher (see e.g., Capson, et al., 1992. Kinetic characterization of the polymerase and exonuclease activity of the gene 43 protein of bacteriophage T4. *Biochemistry* 31: 10984–10994). Although a very high fidelity can be achieved by using polymerases with inherent exonuclease activity, their use also holds the disadvantage that primer degradation may occur.

Although the exonuclease activity of the Klenow fragment of DNA polymerase I (Klenow) is low, it has been demonstrated that the 3'-terminus of a primer may be degraded with longer incubations in the absence of nucleotide triphosphates (see e.g., Ronaghi, et al., 1998. *Doctoral Dissertation*, The Royal Institute of Technology, Dept. of Biochemistry (Stockholm, Sweden)). Fidelity is maintained without exonuclease activity because an induced-fit binding mechanism in the polymerization step provides a very efficient selectivity for the correct dNTP. Fidelities of $1 \times 10^5$ to $1 \times 10^6$ have been reported (see e.g., Wong, et al., 1991. An induced-fit kinetic mechanism for DNA replication fidelity. *Biochemistry* 30: 526–537). In pyrophosphate sequencing, exonuclease-deficient (exo-) polymerases, such as exo-Klenow or Sequenase®, have been confirmed to have high fidelity.

Estimates for the spatial and temporal constraints on the pyrophosphate sequencing methodology of the present invention have been calculated, wherein the instant system possesses a 1 cm² area with height approximately 50 μm, for a total volume of 5 μl. With respect to temporal constraints, the molecular species participating in the cascade of reactions are initially defined, wherein:

N=the DNA attached to the surface
$PP_i$=the pyrophosphate molecule released
ATP=the ATP generated from the pyrophosphate
L=the light released by luciferase It is further specified that N(0) is the DNA with no nucleotides added, N(1) has 1 nucleotide added, N(2) has 2 nucleotides added, and so on. The pseudo-first-order rate constants which relate the concentrations of molecular species are:

| | |
|---|---|
| $N(n) \rightarrow N(n + 1) + PP_i$ | $k_N$ |
| $PP_1 \rightarrow ATP$ | $k_P$ |
| $ATP \rightarrow L$ | $k_A$ |

In addition, the diffusion constants $D_P$ for $PP_i$ and $D_A$ for ATP must also be specified. These values may be estimated from the following exemplar diffusion constants for biomolecules in a dilute water solution (see Weisiger, 1997. Impact of Extracellular and Intracellular Diffusion on Hepatic Uptake Kinetics Department of Medicine and the Liver Center, University of California, San Francisco, Calif., USA, dickw@itsa.ucsf.edu, http://dickw.ucsf.edu/papers/goresky97/chapter.html).

| Molecule | D/10⁻⁵ cm²/sec | Method | Original Reference |
|---|---|---|---|
| Albumin | 0.066 | lag time | 1 |
| Albumin | 0.088 | light scattering | 2 |
| Water | 1.940 | NMR | 3 | wherein, Original Reference 1 is: Longsworth, 1954. Temperature dependence of diffusion in aqueous solutions, *J. Phys. Chem.* 58: 770–773; Original Reference 2 is: Gaigalas, et al., 1992. Diffusion of bovine serum albumin in aqueous solutions, *J. Phys. Chem.* 96: 2355–2359; and Original Reference 3 is: Cheng, 1993. Quantitation of non-Einstein diffusion behavior of water in biological tissues by proton NMR diffusion imaging: Synthetic image calculations, *Magnet. Reson. Imaging* 11: 569–583.

In order to estimate the diffusion constant of $PP_i$, the following exemplar values may be utilized (see *CRC Handbook of Chemistry and Physics*, 1983. (W. E. Weast. Ed.) CRC Press, Inc., Boca Raton, Fla.):

| Molecule | D/10⁻⁵ cm²/sec | Molecular Weight/amu |
|---|---|---|
| sucrose | 0.5226 | 342.30 |
| mannitol | 0.682 | 182.18 |
| penta-erythritol | 0.761 | 136.15 |
| glycolamide | 1.142 | N/A |
| glycine | 1.064 | 75.07 |

The molecular weight of $PP_i$ is 174 amu. Based upon the aforementioned exemplar values, a diffusion constant of approximately $0.7 \times 10^{-5}$ cm²/sec for $PP_i$ is expected.

Enzymes catalyzing the three pyrophosphate sequencing reactions are thought to approximate Michaelis-Menten kinetics (see e.g. Stryer, 1988. *Biochemistry*, W. H. Freeman and Company, New York), which may be described:

$K_M=[E][S]/[ES]$, velocity=$V_{max}[S]/(K_M+[S])$, $V_{max}=k_{turnover}[E_T]$ where [S] is the concentration of substrate, [E] is the concentration of free enzyme, [ES] is the concentration of the enzyme-substrate complex, and $[E_T]$ is the total concentration of enzyme=[E]+[ES].

It is preferable that the reaction times are at least as fast as the solution-phase pyrophosphate-based sequencing described in the literature. That rate that a substrate is converted into product is $-d[S]/dt=K_{turnover}[E_T][S]/(K_M+[S])$ The effective concentration of substrate may be estimated from the size of a replicated DNA molecule, at most (10 μm)³ and the number of copies (approximately 10,000), yielding a concentration of approximately 17 nM. This is this is smaller than the $K_M$ for the enzymes described previously, and therefore the rate can be estimated to be $-d[S]/dt=(K_{turnover}/K_M)[E_T][S]$.

Thus, with pseudo first-order kinetics, the rate constant for disappearance of substrate depends on $K_{turnover}$ and $K_M$, which are constants for a given enzyme, and $[E_T]$. Using the same enzyme concentrations reported in the literature will therefore produce similar rates.

The first step in the pyrophosphate sequencing reaction (i.e., incorporation of a new nucleotide and release of $PP_i$) will now be examined in detail. The preferred reaction conditions are: 1 pmol DNA, 3 pmol polymerase, 40 pmol dNTP in 0.2 ml buffer. Under the aforementioned, preferred reaction conditions, the $K_M$ for nucleotide incorporation for the Klenow fragment of DNA polymerase I is 0.2 μM and for Sequenase 2.0™ (US Biochemicals, Cleveland, Ohio) is 0.4 μM, and complete incorporation of 1 base is less than 0.2 sec (see e.g., Ronaghi, et al., 1996. Real-Time DNA Sequencing Using Detection of Pyrophosphate Release, *Anal. Biochem.* 242: 84–89) with a polymerase concentration of 15 nM.

In a 5 μl reaction volume, there are a total of 10,000 anchor primers with 10,000 sequencing primer sites each, or $1 \times 10^8$ total extension sites=0.17 fmol. Results which have been previously published in the literature suggest that polymerase should be present at 3-times abundance, or a 0.5 fmol, within the reaction mixture. The final concentration of polymerase is then 0.1 nM. It should be noted that these reaction conditions are readily obtained in the practice of the present invention.

As previously stated, the time required for the nucleotide addition reaction is no greater than 0.2 sec per nucleotide. Hence, if the reaction is allowed to proceed for a total of T seconds, then nucleotide addition should be sufficiently rapid that stretches of up to (T/0.2) identical nucleotides should be completely filled-in by the action of the polymerase. As will be discussed infra, the rate-limiting step of the pyrophosphate sequencing reaction is the sulfurylase reaction, which requires a total of approximately 2 sec to complete. Accordingly, a total reaction time which allows completion of the sulfurylase reaction, should be sufficient to allow the polymerase to "fill-in" stretches of up to 10 identical nucleotides. In random DNA species, regions of 10 or more identical nucleotides have been demonstrated to occur with a per-nucleotide probability of approximately $4^{-10}$, which is approximately $1 \times 10^{-6}$. In the 10,000 sequences which are extended from anchor primers in a preferred embodiment of the present invention, each of which will be extended at least 30 nt. and preferably 100 nt., it is expected that approximately one run of 10 identical nucleotides will be present. Thus, it may be concluded that runs of identical nucleotides should not pose a difficulty in the practice of the present invention.

The overall size of the resulting DNA molecule is, preferably, smaller than the size of the anchoring pads (i.e., 10 µm) and must be smaller than the distance between the individual anchoring pads (i.e., 100 µm). The radius of gyration of a single-stranded DNA concatemer with N total nucleotides may be mathematically-estimated by the following equation: radius=$b (N/N_0)^{0.6}$, where b is the persistence length and No is the number of nucleotides per persistence length; the exponent 0.6 is characteristic of a self-avoiding walk (see e.g., Doi, 1986. *The Theory of Polymer Dynamics* (Clarendon Press, New York); Flory, 1953. *Principles of Polymer Chemistry* (Cornell University Press, New York)). Using single-stranded DNA as an example, b is 4 mm and $N_0$ is 13.6 nt. (see e.g., Grosberg, 1994. *Statistical Physics of Macromolecules* (AIP Press, New York)). Using 10,000 copies of a 100-mer, $N=1 \times 10^6$ and the radius of gyration is 3.3 µm.

The sulfurylase reaction will now be discussed in detail. The time for the production of ATP from adenosine 5'-phosphosulfate (APS) and $PP_i$ has been estimated to be less than 2 sec (see e.g., Nyrén and Lundin, 1985. *Anal. Biochem.* 151: 504–509. The reported reaction conditions for 1 pmol $PP_i$ in 0.2 ml buffer (5 nM) are 0.3 U/ml ATP sulfurylase (ATP:sulfate adenylyltransferase; Prod. No. A8957; Sigma Chemical Co., St. Louis, Mo.) and 5 µM APS (see e.g., Ronaghi, et al., 1996. Real-Time DNA Sequencing Using Detection of Pyrophosphate Release, *Anal. Biochem.* 242: 84–89). The manufacturer's information (Sigma Chemical Co., St. Louis, Mo.) for sulfurylase reports an activity of 5–20 units per mg protein (i.e., one unit will produce 1.0 µmole of ATP from APS and PPi per minute at pH 8.0 at 30 C), whereas the specific activity has been reported elsewhere as 140 units per mg (see Karamohamed, et al., 1999. Purification, and Luminometric Analysis of Recombinant *Saccharomyces cerevisiae* MET3 Adenosine Triphosphate Sulfurylase Expressed in *Escherichia coli*, *Prot. Express. Purification* 15: 381–388). Due to the fact that the reaction conditions utilized in the practice of the present invention are similar to those reaction conditions reported in the aforementioned reference, the sulfurylase concentration within the assay was estimated as 4.6 nM. Thus, at the half-maximal rate, [APS]=0.5 µM and $[PP_i]$=7 µM.

In the reaction conditions utilized in the present invention, $[PP_i]$ is approximately 0.17 fmol in 5 µl, or 0.03 nM. The fraction of $PP_i$ which is bound to the enzyme is $[E]/K_M$, where [E] is the concentration of free enzyme. Since the enzyme concentration is much larger than the $PP_i$ concentration, the total enzyme concentration alone, may be used in the calculations. The fraction of $PP_i$ bound to enzyme is found to be 4.6 nM/7 µM=$7 \times 10^{-4}$. Therefore, it may be concluded that the $PP_i$ spends most of its time freely diffusing before being converted to ATP.

The mean time for each PPi to react is $1/k_P$=2 seconds. The mean square distance it diffuses in each direction is approximately $2D_P/k_P$, or $2.8 \times 10^3$ µm². The RMS distance in each direction is 53 µm. This value indicates that each of the individual anchor primers must be more than 50 µm apart, or $PP_i$ which is released from one anchor could diffuse to the next, and be detected.

Another method which may be used to explain the aforementioned phenomenon is to estimate the amount of $PP_i$ over a first anchor pad that was generated at said first anchor pad relative to the amount of $PP_i$ that was generated at a second anchor pad and subsequently diffused over to the location of said first anchor pad. When these two quantities approach each other in magnitude, it becomes difficult to distinguish the "true" signal from that of the background. This may be mathematically-described by defining a as the radius of an anchor pad and $1/b^2$ as the density of an anchor pad. Based upon previously published data, a is approximately equal to 10 µm and b is approximately equal to 100 µm. The amount of $PP_i$ which is present over said first anchor pad may be described by: $\exp(-k_P t)[1-\exp(-a^2/2D_P t)]$ and the amount of $PP_i$ present over the second anchor pads may be mathematically-approximated by: $(\frac{1}{3})\exp(-k_P t)[pa^2/b^2]\exp(-b^2/2D_P t)$. The prefactor ⅓ assumes that ¼ of the DNA sequences will incorporate 1 nucleotide, ¼ of these will then incorporate a second nucleotide, etc., and thus the sum of the series is ⅓. The amounts of PPi over the first and second anchor pads become similar in magnitude when $2D_P t$ is approximately equal to $b^2$, thus indicating that the RMS distance a molecule diffuses is equal to the distance between adjacent anchor pads. In accord, based upon the assay conditions utilized in the practice of the present invention, the anchor pads must be placed no closer than approximately 50 µm apart, and preferable are at least 3-times further apart (i.e., 150 µm).

Although the aforementioned findings set a limit on the surface density of anchor pads, it is possible to decrease the distance requirements, while concomitantly increasing the overall surface density of the anchor pads, by the use of a number of different approaches. One approach is to detect only the early light, although this has the disadvantage of losing signal, particularly from DNA sequences which possess a number of contiguous, identical nucleotides.

A second approach to decrease the distance between anchor pads is to increase the concentration of sulfurylase in the reaction mixture. The reaction rate $k_P$ is directly proportional to the sulfurylase concentration, and the diffusion distance scales as $k_P^{1/2}$. Therefore, if the sulfurylase enzyme concentration is increased by a factor of 4-times, the distance between individual anchor pads may be concomitantly reduced by a factor of 2-times.

A third approach is to increase the effective concentration of sulfurylase (which will also work for other enzymes described herein) by binding the enzyme to the surface of the anchor pads. The anchor pad can be approximated as one wall of a cubic surface enclosing a sequencing reaction center. Assuming a 10 μm×10 μm surface for the pad, the number of molecules bound to the pad to produce a concentration of a 1 μM is approximately 600,000 molecules.

The sulfurylase concentration in the assay is estimated as 5 nM. The number of bound molecules to reach this effective concentration is about 3000 molecules. Thus, by binding more enzyme molecules, a greater effective concentration will be attained. For example, 10,000 molecules could be bound per anchor pad.

As previously estimated, each sulfurylase molecule occupies a total area of 65 $nM^2$ on a surface. Accordingly, anchoring a total of 10,000 sulfurylase enzyme molecules on a surface (i.e., so as to equal the 10,000 $PP_i$ released) would require 1.7 $μm^2$. This value is only approximately 2% of the available surface area on a 10 μm×10 μm anchor pad. Hence, the concentration of the enzyme may be readily increased to a much higher value.

A fourth approach to allow a decrease in the distance between individual anchor pads, is to utilize one or more agents to increase the viscosity of the aqueous-based, pyrophosphate sequencing reagents (e.g., glycerol, polyethylene glycol (PEG), and the like) so as to markedly increase the time it takes for the PPi to diffuse. However, these agents will also concomitantly increase the diffusion time for other non-immobilized components within the sequencing reaction, thus slowing the overall reaction kinetics. Additionally, the use of these agents may also function to chemically-interfere with the sequencing reaction itself.

A fifth, and preferred, methodology to allow a decrease in the distance between individual anchor pads, is to conduct the pyrophosphate sequencing reaction in a spatial-geometry which physically-prevents the released $PP_i$ from diffusing laterally. For example, uniform cavities, which are generated by acid-etching the termini of optical fiber bundles, may be utilized to prevent such lateral diffusion of PPi (see Michael, et al., 1998. Randomly Ordered Addressable High-Density Optical Sensor Arrays, *Anal. Chem.* 70: 1242–1248). In this embodiment, the important variable involves the total diffusion time for the $PP_i$ to exit a cavity of height h, wherein h is the depth of the etched cavity. This diffusion time may be calculated utilizing the equation: $2D_pt=h^2$. By use of the preferred pyrophosphate sequencing reaction conditions of the present invention in the aforementioned calculations, it may be demonstrated that a cavity 50 μm in depth would be required for the sequencing reaction to proceed to completion before complete diffusion of the $PP_i$ from said cavity. Moreover, this type of geometry has the additional advantage of concomitantly reducing background signal from the $PP_i$ released from adjacent anchor pads. In contrast to use of a "chip"-based geometry, wherein the required sequencing reagents are "flowed" over the surface of the solid support matrix (i.e., the anchor pads), delivery of the various sequencing reagents in acid-etched optical fiber bundle embodiment is performed by immersion of the acid-etched cavities, alternately, into dNTP/APS/sulfurylase reagents and then, subsequently, into the apyrase reagents to facilitate the degradation of any remaining dNTPs.

Subsequently, once ATP has been formed by use of the preferred reaction conditions of the present invention, the reaction time, $1/k_4$, has been shown to be 0.2 seconds. Because this reaction time is much lower than the time which the $PP_i$ is free to diffuse, it does not significantly alter any of the aforementioned conclusions regarding the assay geometry and conditions utilized in the present invention.

In order to mitigate the generation of background light, it is preferable to "localize" (e.g., by anchoring or binding) the luciferase in the region of the DNA sequencing templates. It is most preferable to localize the luciferase to a region that is delineated by the distance a $PP_i$ molecule can diffuse before it forms ATP. Methods for binding luciferase to a solid support matrix are well-known in the literature (see e.g., Wang, et al., 1997. Specific Immobilization of Firefly Luciferase through a Biotin Carboxyl Carrier Protein Domain, *Analytical Biochem.* 246: 133–139). Thus, for a 2 second diffusion time, the luciferase is anchored within a 50 μm distance of the DNA strand. It should be noted, however, that it would be preferable to decrease the diffusion time and thus to further limit the surface area which is required for luciferase binding.

In order to determine the concentration of luciferase which it is necessary to bind, previously published conditions were utilized in which luciferase is used at a concentration which gives a response of 200 mV for 0.1 μm ATP (see Ronaghi, et al., 1996. Real-Time DNA Sequencing Using Detection of Pyrophosphate Release, *Analytical Biochem.* 242: 84–89). More specifically, it is known from the literature that, in a 0.2 ml reaction volume, 2 ng of luciferase gives a response of 10 mV for 0.1 μM ATP (see Karamohamed and Nyrén, 1999. Real-Time Detection and Quantification of Adenosine Triphosphate Sulfurylase Activity by a Bioluminometric Approach, *Analytical Biochem.* 271: 81–85). Accordingly, a concentration of 20 ng of luciferase within a 0.2 ml total reaction volume would be required to reproduce these previously-published literature conditions. In the volume of a 10 μm cube around each of the individual anchor pads of the present invention, a luciferase concentration of $1×10^{-16}$ grams would be required, and based upon the 71 kD molecular weight of luciferase, this concentration would be equivalent to approximately 1000 luciferase molecules. As previously stated, the surface area of luciferase has been computed at 50 $nm^2$. Thus, assuming the luciferase molecules were biotinylated and bound to the anchor pad, 1000 molecules would occupy a total area of 0.05 $μm^2$. From these calculations it becomes readily apparent that a plethora of luciferase molecules may be bound to the anchor pad, as the area of each anchor pad area is 100 $μm^2$.

Again, based upon previously-published results in the literature, each nucleotide takes approximately 3 seconds in toto, to sequence (i.e., 0.5 seconds to add a nucleotide; 2 seconds to make ATP; 0.2 seconds to get fluorescence). Accordingly, a cycle time of approximately 60 seconds per nucleotide is reasonable, requiring approximately 30 minutes per experiment to generate 30 nucleotides of information per sequencing template.

In an alternative embodiment to the aforementioned sequencing methodology (i.e., polymerase→$PP_i$→sulfurylase→ATP→luciferase→light cascade), a polymerase may be developed (e.g., through the use of protein fusion and the like) which possesses the ability to generate light when it incorporates a nucleotide into a growing DNA chain. In yet another alternative embodiment, a sensor may be developed which directly measures the production of $PP_i$ in the sequencing reaction. As the production of $PP_i$ changes the electric potential of the surrounding buffer, this change could be measured and calibrated to quantify the concentration of $PP_i$ produced.

As previously discussed, the polymerase-mediated incorporation of dNTPs into the nucleotide sequence in the pyrophosphate sequencing reaction causes the release of an inorganic pyrophosphate (PPi) moiety which, in turn, through catalysis by luciferase, causes the release of a photon (i.e., light). The photons generated by the pyrophosphate sequencing reaction may subsequently be "captured"

and quantified by a variety of methodologies including, but not limited to: a photomultiplier tube, CCD, absorbance photometer, a luminometer, and the like.

The photons generated by the pyrophosphate sequencing reaction are captured by the CCD only if they pass through a focusing device (e.g., an optical lens or optical fiber) and are focused upon a CCD element. The fraction of these photons which are captured may be estimated by the following calculations. First, it is assumed that the lens that focuses the emitted photons is at a distance r from the surface of the solid surface (i.e., DNA chip or etched fiber optic well), where r=1 cm, and that the photons must pass through a region of diameter b (area=$\pi b^2/4$) so as to be focused upon the array element, where b=100 μm. It should also be noted that the emitted photons should escape equally in all directions. At distance r, the photons are dispersed over an area of which is equal to $4\pi r^2$. Thus, the fraction of photons which pass through the lens is described by: $(\frac{1}{2})[1-(1+b^2/4r^2)-^{1/2}]$. When the value of r is much larger than that of b, the fraction which pass through the lens may then be described by: $b^2/16r^2$. For the aforementioned values of r and b, this fraction of photons is $6\times10^{-6}$.

For each nucleotide addition, it is expected that approximately 10,000 $PP_i$ molecules will be generated and, if all are converted by sulfurylase and luciferase, these PPi will result in the emission of approximately $1\times10^4$ photons. In order to maximize their subsequent "capture" and quantitation when utilizing a planar array (e.g., a DNA chip), it is preferable to collect the photons immediately at the planar solid support (e.g., the cover slip). This may be accomplished by either: (i) utilizing optical immersion oil between the cover slip and a traditional optical lens or optical fiber bundle or, preferably, (ii) incorporating optical fibers directly into the cover slip itself. Performing the previously described calculations (where in this case, b=100 μm and r=50 μm), the fraction collected is found to be 0.15, which equates to the capture of approximately $1\times10^3$ photons. This value would be sufficient to provide an adequate signal.

The following examples are meant to illustrate, not limit, the invention.

EXAMPLE 1

Construction of Anchor Primers Linked to a Cavitated Terminus Fiber Optic Array

The termini of a thin wafer fiber optic array are cavitated by inserting the termini into acid as described by Healey et al., *Anal. Chem.* 69: 2213–2216 (1997).

A thin layer of a photoactivatable biotin analog is dried onto the cavitated surface as described Hengsakul and Cass (*Bioconjugate Chem.* 7: 249–254, 1996) and exposed to white light through a mask to create defined pads, or areas of active biotin. Next, avidin is added and allowed to bind to the biotin. Biotinylated oligonucleotides are then added. The avidin has free biotin binding sites that can anchor biotinylated oligonucleotides through a biotin-avidin-biotin link.

The pads are approximately 10 μm on a side with a 100 μm spacing. Oligonucleotides are added so that approximately 37% of the pads include one anchored primer. On a 1 cm surface are deposited 10,000 pads, yielding approximately 3700 pads with a single anchor primer. Sulfurylase, apyrase, and luciferase are also attached to the cavitated substrate using biotin-avidin.

EXAMPLE 2

Annealing and Amplification of Members of a Circular Nucleic Acid Library

A library of open circle library templates is prepared from a population of nucleic acids suspected of containing a single nucleotide polymorphism on a 70 bp Sau3A1-MspI fragment. The templates include adapters that are complementary to the anchor primer, a region complementary to a sequencing primer, and an insert sequence that is to be characterized. The library is generated using Sau3A1 and MspI to digest the genomic DNA. Inserts approximately 65–75 nucleotides are selected and ligated to adapter oligonucleotides 12 nucleotides in length. The adapter oligonucleotides have sequences complementary to sequences to an anchor primers linked to a substrate surface as described in Example 1.

The library is annealed to the array of anchor primers. A DNA polymerase is added, along with dNTPs, and rolling circle replication is used to extend the anchor primer. The result is a single DNA strand, still anchored to the solid support, that is a concatenation of multiple copies of the circular template. 10,000 or more copies of circular templates in the hundred nucleotide size range.

EXAMPLE 3

Sequence Analysis of Nucleic Acid Linked to the Terminus of a Fiber Optic Substrate The fiber optic array wafer containing amplified nucleic acids as described in Example 2 is placed in a perfusion chamber and attached to a bundle of fiber optic arrays, which are themselves linked to a 16 million pixel CCD cameras. A sequencing primer is delivered into the perfusion chamber and allowed to anneal to the amplified sequences.

The sequencing primer primes DNA synthesis extending into the insert suspected of having a polymorphism, as shown in FIG. 1. The sequencing primer is first extended by delivering into the perfusion chamber, in succession, a wash solution, a DNA polymerase, and one of dTTP, dGTP, dCTP, or αdATP (a dATP analog). The sulfurylase, luciferase, and apyrase, attached to the termini convert any PPi liberated as part of the sequencing reaction to detectable light. The apyrase present degrades any unreacted dNTP. Light is typically allowed to collect for 3 seconds (although 1–100, e.g., 2–10 seconds is also suitable) by a CCD camera linked to the fiber imaging bundle, after which additional wash solution is added to the perfusion chamber to remove excess nucleotides and byproducts. The next nucleotide is then added, along with polymerase, thereby repeating the cycle.

During the wash the collected light image is transferred from the CCD camera to a computer. Light emission is analyzed by the computer and used to determine whether the corresponding dNTP has been incorporated into the extended sequence primer. Addition of dNTPs and pyrophosphate sequencing reagents is repeated until the sequence of the insert region containing the suspected polymorphism is obtained. Optionally, the sequencing primer is annealed to the amplified sequences before they are bound to the wafer.

EXAMPLE 4

Sequence Analysis of a Tandem Repeat Template Generated Using Rolling Circle Amplification A primer having the sequence 5'-gAC CTC ACA CgA Tgg CTg CAg CTT-3' (SEQ ID NO:2) was annealed to a 88 nucleotide template molecule having the sequence 5'-TCg TgT gAg gTC TCA gCA TCT TAT gTA TAT TTA CTT CTA TTC TCA gTT gCC TAA gCT gCA gCC A-3' (SEQ ID NO:8). Annealing of the template to the primer resulted in juxtaposition of the 5' and 3' ands of the template molecule. The annealed template was exposed to ligase, which resulted in ligation of the 5' and 3' ends of the template to generate a circular molecule.

The annealed primer was extended using Klenow fragment and nucleotides in rolling circle amplification for 12 hours at 12 hours at 37° C. The product was purified using SPRI beads (Seradyne, Indianapolis, Ind.). Rolling circle amplification resulted in formation of tandem repeats of a sequence complementary to the circular template sequence.

The tandem repeat product in the extended sequence was identified by annealing a sequencing primer having the sequence 5'-AAgCTgCAgCCATCgTgTgAgg-3' (SEQ ID NO:8) and subjecting the annealed primer to 40 alternating cycles of 95° C., 1 minute, 20 seconds, 60° C. using ET terminator chemistry (Amersham-Pharmacia) in the presence of 1M betaine.

The sequencing product was then diluted to ⅕ volume and purified on a G-50 Sephadex column prior to injection into a MegaBACE sequencing system with linear polyacrylamide (Amersham-Pharmacia).

Figure 5:
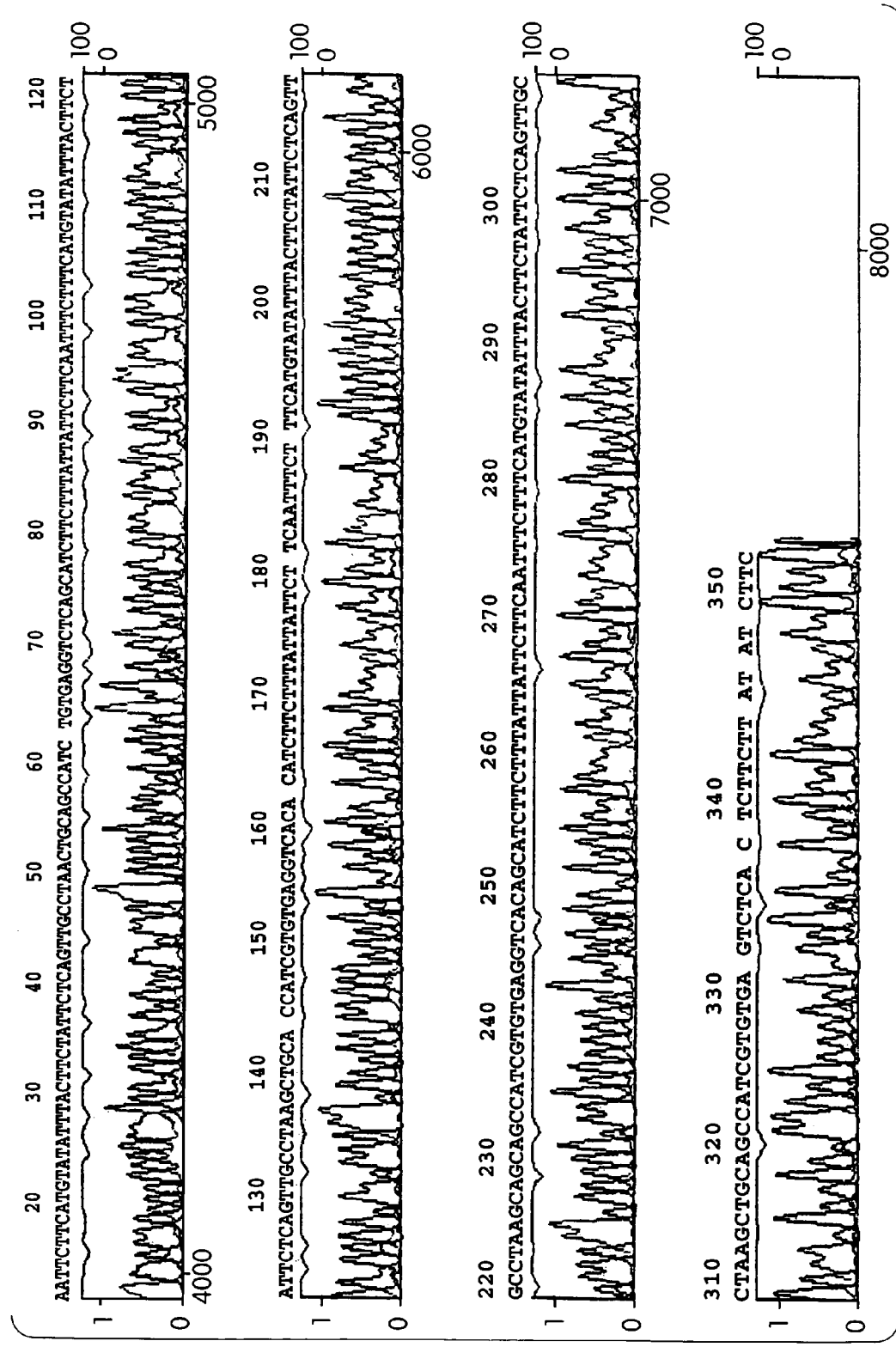
FIG. 5 is a tracing of a sequence output of a concatemeric template generated using rolling circle amplification.

An electropherogram of the sequencing analysis is shown in FIG. 5. The tracing demonstrates that multiple copies of the 88 bp circular template molecule are generated tandemly, and that these copies can be detected in a DNA sequencing reaction.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for sequencing a nucleic acid, the method comprising:
providing a substrate which comprises: a cavitated fiber optic wafer formed from a fused bundle of a plurality of individual optical fibers, each individual optical fiber having a diameter between 3 and 100 μm, the wafer comprising a top surface and a bottom surface, the top surface comprising at least 10,000 wells, wherein said wells are etched into the top surface of the cavitated fiber optic wafer and wherein the thickness of the wafer between the top surface and the bottom surface is between 0.5 mm and 5.0 mm in thickness; wherein the depth of each well ranges from between one half the diameter of an individual optical fiber and three times the diameter of an individual optical fiber; and wherein a plurality of wells on the top surface of the cavitated wafer have a nucleic acid therein; and a plurality of beads within wells on the top surface of the cavitated wafer, said beads having a pyrophosphate sequencing reagent attached thereto;
delivering additional pyrophosphate sequencing reagents, including sequential delivery of nucleotide triphosphates, from one or more reservoirs to the flow chamber so the beads and nucleic acids in the wells on the top surface of the fiber optic wafer are exposed to the reagents; and
detecting optical signals from each well using a detection means that is in communication with the wells, each optical signal being indicative of reaction of the pyrophosphate sequencing reagents with the nucleic acid in a well, thereby sequencing the nucleic acid.

2. The method of claim 1, wherein the nucleic acid is immobilized on said wells or beads.

3. The method of claim 1, wherein the-nucleic acid is DNA.

4. The method of claim 1, wherein the-nucleic acid is genomic DNA or cDNA.

5. The method of claim 1, wherein the nucleic acid is 10–1000 nucleotides in length.

6. The method of claim 1, wherein pyrophosphate is produced as a sequencing byproduct.

7. The method of claim 6, wherein the pyrophosphate is detected by contacting the sequencing byproduct with a sulfurylase under conditions that allow formation of ATP.

8. The method of claim 7, wherein the sulfurylase is a thermostable sulfurylase.

9. The method of claim 6, further comprising adding apyrase to degrade unreacted nucleotide triphosphates.

10. The method of claim 6, further comprising washing the top surface of the fiber optic wafer with a buffer between each delivery of the nucleotide triphosphates.

11. The method of claim 10, wherein the-buffer includes apyrase.

12. The method of claim 1, wherein the diameter of each individual optical fiber in the cavitated wafer is between 6–50 μm.

13. The method of claim 1, wherein the nucleic acid is sequenced in the presence of a dATP analog.

14. The method of claim 13, wherein the dATP analog is a thio ATP.

15. The method of claim 1, wherein the fiber optic surface includes two or more nucleic acids separated by approximately 10 μm to approximately 200 μm.

16. The method of claim 15, wherein the fiber optic surface includes two or more nucleic acids separated by approximately 50 μm to approximately 150 μm.

17. The method of claim 15, wherein the fiber optic surface includes two or more nucleic acids separated by approximately 100 μm to approximately 150 μm.

18. The method of claim 15, wherein the fiber optic surface includes two or more nucleic acids separated by approximately 150 μm.

19. The method of claim 1, wherein said detection means is a CCD camera.

20. The method of claim 1, wherein the substrate has a polished fiber optic surface opposite to the cavitated fiber optic surface.

21. The method of claim 20, wherein the polished surface allows for optical coupling to a second optical fiber.

22. The method of claim 1, wherein the cavitated fiber optic wafer is coated.

23. The method of claim 22, wherein the coating is selected from the group consisting of plastic, gold layers, organosilane reagents, photoreactive linkers, hydrophilic polymer gels and pluronic polymers.

24. The method of claim 1, wherein said pyrophosphate sequencing reagent is luciferase.

25. The method of claim 1, wherein said pyrophosphate sequencing reagent is sulfurylase.

26. The method of claim 1, wherein said substrate further comprises $10^3$ or more nucleic acids in said wells.

27. The method of claim 1, wherein said substrate comprises $10^4$ or more nucleic acids in said wells.

28. The method of claim 1, wherein said substrate comprises $10^5$ or more nucleic acids in said wells.

29. The method of claim 26, wherein the nucleic acids are attached to the wells or beads by a linker.

30. The method of claim 26, wherein the nucleic acids are covalently attached to the wells or beads.

* * * * *

SEQUENCE LISTING

<160> NUMBER OF SEQ ID NOS: 9

<210> SEQ ID NO 1
<211> LENGTH: 64
<212> TYPE: DNA
<213> ORGANISM: Artificial Sequence
<220> FEATURE:
<223> OTHER INFORMATION: Description of Artificial Sequence: putative
      template molecule

<400> SEQUENCE: 1
tcgtgtgagg tctcagcatc ttatgtatat ttacttctat tctcagttgc ctaagctgca      60
gcca                                                                  64

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: putative
      anchor primer

<400> SEQUENCE: 2
gacctcacac gatggctgca gctt                                            24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: generic
      anchor primer

<400> SEQUENCE: 3
gacctcacac gatggctgca gctt                                            24

<210> SEQ ID NO 4
<211> LENGTH: 64

```
<212> TYPE: DNA
<213> ORGANISM: Artificial Sequence
<220> FEATURE:
<223> OTHER INFORMATION: Description of Artificial Sequence: putative
      SNP probe

<400> SEQUENCE: 4
tttatatgta ttctacgact ctggagtgtg ctaccgacgt cgaatccgtt gactcttatc    60
ttca                                                                 64

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: putative
      SNP region

<400> SEQUENCE: 5
ctagctcgta catataaatg aagataagat cctg                                34

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: putative
      anchor primer

<400> SEQUENCE: 6
gacctcacac gagtagcatg gctgcagctt                                     30

<210> SEQ ID NO 7
<211> LENGTH: 64
<212> TYPE: DNA
<213> ORGANISM: Artificial Sequence
<220> FEATURE:
<223> OTHER INFORMATION: Description of Artificial Sequence: putative
      template molecule

<400> SEQUENCE: 7
tcgtgtgagg tctcagcatc ttatgtatat ttacttctat tctcagttgc ctaagctgca    60
gcca                                                                 64

<210> SEQ ID NO 8
<211> LENGTH: 64
<212> TYPE: DNA
<213> ORGANISM: Artificial Sequence
<220> FEATURE:
<223> OTHER INFORMATION: Description of Artificial Sequence: putative
      template molecule

<400> SEQUENCE: 8
tcgtgtgagg tctcagcatc ttatgtatat ttacttctat tctcagttgc ctaagctgca    60
gcca                                                                 64

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: putative
      sequencing primer
```

```
<400> SEQUENCE: 9
aagctgcagc catcgtgtga gg                                              22
```